(12) United States Patent
Seong et al.

(10) Patent No.: US 9,272,047 B2
(45) Date of Patent: Mar. 1, 2016

(54) USE OF BIOLOGICAL SURFACTANT AS ANTI-INFLAMMATORY AGENT AND TISSUE PRESERVATIVE SOLUTION

(75) Inventors: Seung-yong Seong, Seoul (KR); Chang Gu Kang, Seoul (KR); Youn Hee Kim, Seoul (KR)

(73) Assignee: Shaperon Inc., Seoul (KR)

( * ) Notice: Subject to any disclaimer, the term of this patent is extended or adjusted under 35 U.S.C. 154(b) by 981 days.

(21) Appl. No.: 12/619,644

(22) Filed: Nov. 16, 2009

(65) Prior Publication Data

US 2010/0267684 A1 Oct. 21, 2010

Related U.S. Application Data

(63) Continuation-in-part of application No. PCT/KR2008/002698, filed on May 14, 2008.

(30) Foreign Application Priority Data

May 14, 2007 (KR) .................. 10-2007-0046579

(51) Int. Cl.
*A61K 31/575* (2006.01)
*A61K 47/48* (2006.01)

(52) U.S. Cl.
CPC ......... *A61K 47/48038* (2013.01); *A61K 31/575* (2013.01)

(58) Field of Classification Search
CPC ..................................................... A61K 31/575
USPC ........................................................ 514/183
See application file for complete search history.

(56) References Cited

U.S. PATENT DOCUMENTS

2005/0214360 A1 * 9/2005 Ishibashi ..................... 424/451
2008/0132450 A1 * 6/2008 Lee et al. ...................... 514/12
2008/0220003 A1 * 9/2008 Schnatbaum et al. ..... 424/178.1

* cited by examiner

*Primary Examiner* — Zohreh Fay
(74) *Attorney, Agent, or Firm* — Novick, Kim & Lee, PLLC; Jae Youn Kim

(57) ABSTRACT

The present invention relates to a use of a biological surfactant as an anti-inflammatory agent and a tissue preservative solution. More particularly, the present invention is directed to an anti-inflammatory agent and a tissue preservative solution comprising a biological surfactant which blocks a reaction of a proinflammatory factor with a receptor by emulsifying the proinflammatory factor.

3 Claims, 47 Drawing Sheets

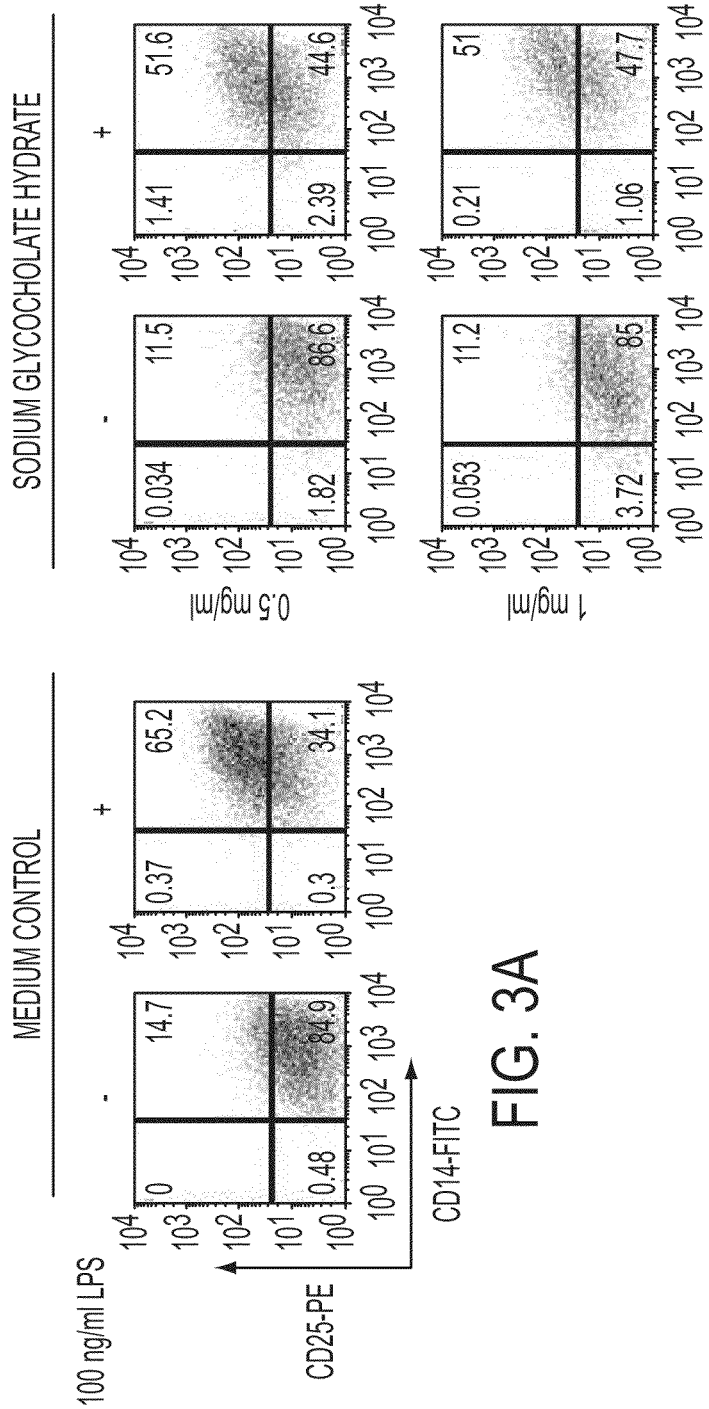

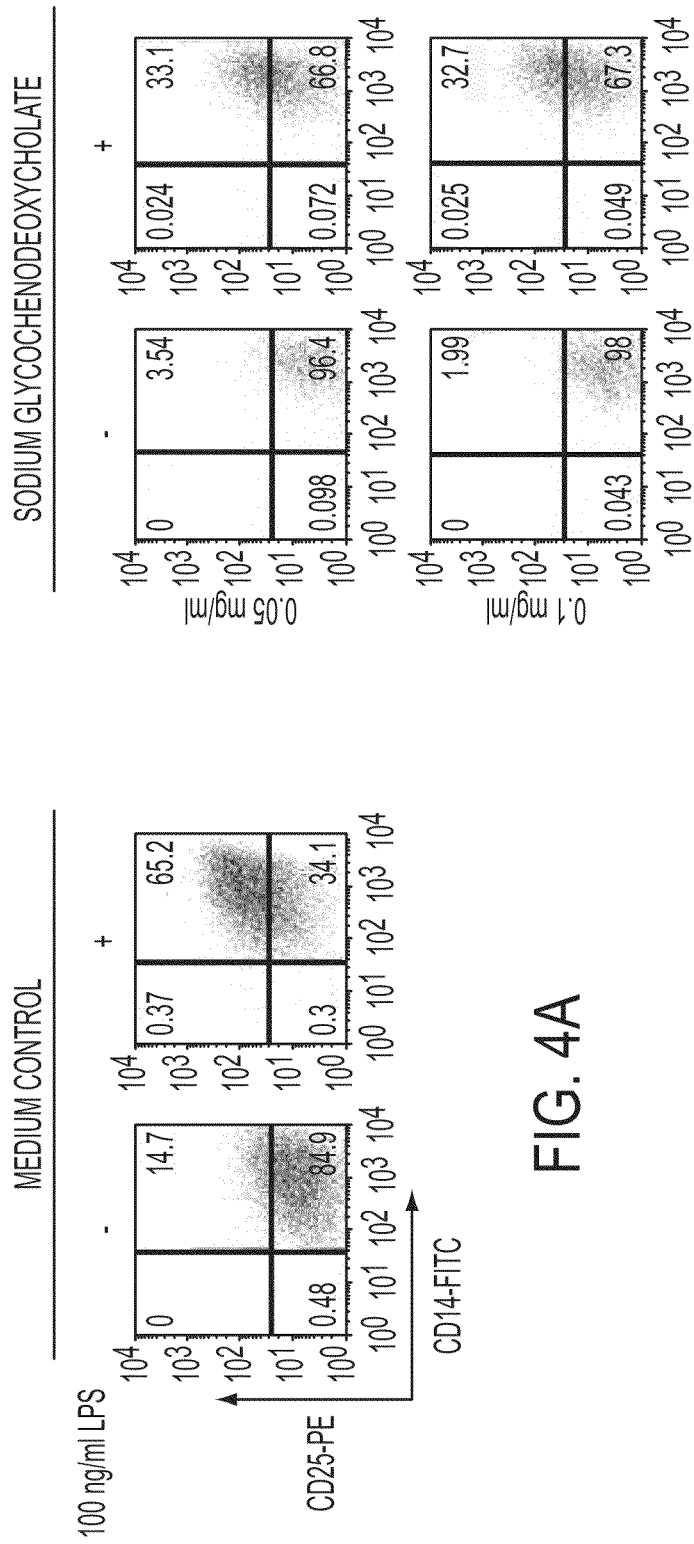

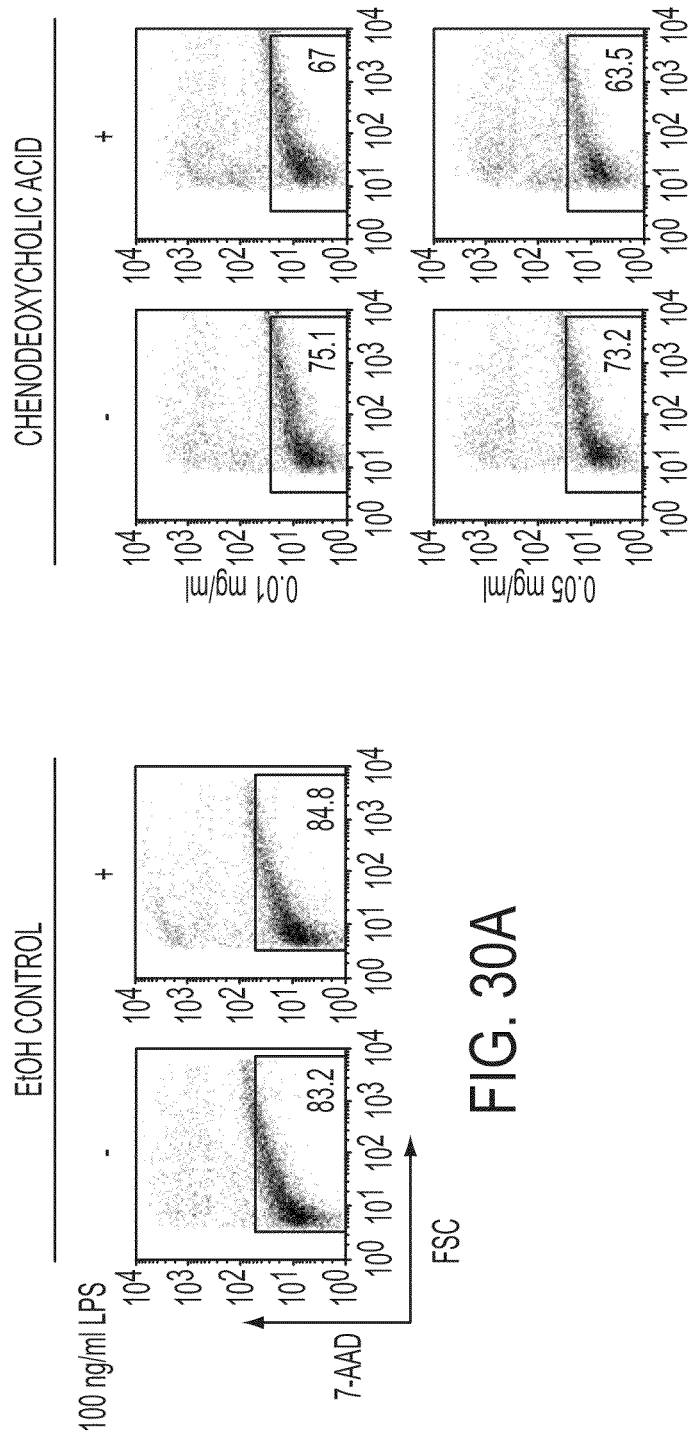

USE OF BIOLOGICAL SURFACTANT AS ANTI-INFLAMMATORY AGENT AND TISSUE PRESERVATIVE SOLUTION

CROSS-REFERENCE TO RELATED APPLICATIONS

The present Application is a Continuation- in- part of PCT/KR2008/002698 filed on May 14, 2008 ("PCT Application"), which claims priority from Korean Application No. KR 10-2007- 0046579 filed on May 14, 2007, both of which are hereby incorporated by reference in their entirety into the present Application. Any amendments made in the PCT Application during the international phase are also incorporated herein by reference.

TECHNICAL FIELD

The present invention relates to a use of a biological surfactant as an anti-inflammatory agent and a tissue preservative solution. More particularly, the present invention is directed to an anti-inflammatory agent and a tissue preservative solution comprising a biological surfactant which blocks a reaction of a proinflammatory factor with a receptor by emulsifying the proinflammatory factor.

BACKGROUND ART

Innate immunomechanism plays a key role in a first defense against pathogen infection, and recognition and recovery of damaged tissue and is mediated by certain cells such as a macrophage and a dendritic cell, and humoral factors such as a complement system and a clotting system.

Particularly, inflammatory response of the innate immune system is a in vivo defense mechanism caused by bacterial endotoxins and tissue damages, and is accompanied by the increase of inflammatory cells (macrophages, dendritic cells, etc.) and proinflammatory cytokines (interleukine-12, TNF-α, etc.), fervescence, local effusion of tissue fluid, fibroplasia for recovery, etc. The activation of such proinflammatory cells can be confirmed by the proinflammatory cytokine production as well as the expression of nuclear transcription factors which are involved in the regulation of the transcription of inflammatory cell genes, and the expression of co-stimulating molecules (CD40, CD80, CD86) or major histocompatibility complexes (MHCs) which are involved in the activation of the inflammatory cells.

Also, the inflammatory cells including antigen presenting cells (APCs) in the innate immunomechanism induces directly or indirectly the activation of the acquired immunomechanism induced by T-cells and B-cells. The acquired immune response activated by systemic inflammatory response exacerbates inflammatory response as well.

Toxin (endotoxin of exotoxin) is an example of a material which can induce an abnormal activation of the innate immune system and an inflammatory response. Endotoxin such as glycolipid of $E.\ coli$ is an amphiphilic molecule which has both hydrophilic regions and hydrophobic regions such as lipid region, and is a principal material constituting a cell wall of Gram-negative bacteria.

Particularly, it is known that the lipid region of the endotoxin has a strong hydrophobicity and plays an important role in the induction of the cytotoxicity. Therefore, various diseases and conditions are induced by the endotoxin. Sepsis, in particular, can cause serious problems in an emergency room or during an operation.

Sepsis induces a serious inflammation in bloods and various organs as bacterial toxins circulate through blood vessels. Sepsis also causes a variety of symptoms such as pyrexia, vomiting, diarrhea, blood pressure drop, tachypnea, tachycardia, frequent urination, stupor, etc.

Sepsis is the third major cause of death in the developed countries. More than 750,000 people are affected by sepsis annually in the United States, and 9% of total deaths in US die from sepsis.

Exotoxin excreted by Gram-positive or Gram-negative bacteria can also induce an inflammation. The exotoxin is comprised of proteins, and is produced and excreted during the metabolic process of Corynebacterium diphteriae, Clostridium tetani, Clostridium botulinum, etc. Similar exotoxins are produced by dysentery bacillus, streptococcus, etc.

Inflammatory responses through an abnormal innate immunoactivity are rising as important problems in an organ transplatation, and one of the problems is the immunorejection which occurs during transplanting porcine cells to a human. Such immunorejections are activated by tissues damaged during an operation as well as natural antibodies existing in blood, and cause tissue necrosis with a serious inflammatory response.

In particular, organ damages due to ischemic anoxia during the extirpation of an organ from a donor, damage during the preservation of an organ before transplantation, and formation of active oxygen and increase in immune responses after reperfusion, have been rising as an important problem.

Therefore, an organ preservative solution which can minimize damages of the organ to be transplanted and immunorejections, is required. Currently, various commercial organ preservative solutions, for example the University of Wisconsin solution developed by the University of Wisconsin in USA and HTK (Histidine-Tryptophan-Ketoglutarate) solution developed in Germany are available. The organ preservative solution is injected as a perfusate before the extirpation of an organ from a donor, or is used for the preservation of an organ before the transplantation of the organ to a patient. However, the conventional organ preservative solutions have limitations on the suppression of inflammatory responses induced by the organ damaged during the transplantation.

Like this, it is important for various inflammatory diseases as well as an organ transplantation to control inflammatory responses.

The conventional anti-inflammatory agents and immunosuppressive agents having an inflammatory suppression effect have disadvantages that the agents have a topical effect and are required for a continuous administration. The agents also have adverse effects when administering the agents.

Vioxx®, a nonsteroidal anti-inflammatory drug (NSAID), is used for the treatment of arthritis, and however it is reported that Vioxx® increases twice the morbidity of heart disease, according to clinical trials. Consequently, the safety of other drugs having an inflammation inhibition mechanism similar to that of Vioxx® is under investigation.

Steroidal anti-inflammatory drugs also have adverse effects. When these steroidal anti-inflammatory drugs are abused, in vivo disease resistance decreases, and therefore the human body becomes sensitive to take diseases such as diabetes, osteoporosis, etc.

Xigris®, the first commercialized therapeutic agent for sepsis, intervenes in the blood clotting process, and therefore can cause a severe bleeding or apoplexy.

U.S. Pat. Nos. 5,283,236 and 5,658,878 disclose sodium glycocholate and derivatives thereof. However, the above patents disclose a use of sodium glycocholate only as a drug delivery enhancing agent, not as an anti-inflammatory agent.

In addition, M. Katsrma et al. reported, in their study of the enhancement of drug delivery ability in colon, that the colonic absorption of insulin is enhanced when sodium glycocholate or polyethylene oxide is administered together with insulin (International Journal of Pharmaceutics, 2006, pp. 156-162). However, Katsrma et al. do not also disclose the anti-inflammatory effect of sodium glycocholate and derivatives thereof.

Therefore, it has been keenly required for the development of a novel drug which can complement defects of the conventional anti-inflammatory agents and enhance the therapeutic effect of an anti-inflammatory agent on inflammation.

DISCLOSURE

Technical Problem

Therefore, the primary object of the present invention is to provide an anti-inflammatory agent comprising a biological surfactant which blocks a reaction of a proinflammatory factor with a receptor by emulsifying the proinflammatory factor.

Another object of the present invention is to provide an additive for tissue or cell preservative solution comprising at least one biological surfactant selected from the group consisting of cholic acid, chenodeoxycholic acid, deoxycholic acid, lithocholic acid, dehydrocholic acid, a conjugate thereof with glycine or taurine, and a pharmaceutically acceptable salt thereof.

Yet another object of the present invention is to provide a therapeutic agent for sepsis, comprising a biological surfactant which blocks a reaction of a proinflammatory factor with a receptor.

Technical Solution

The abovementioned primary object of the present invention can be achieved by providing an anti-inflammatory agent comprising a biological surfactant which blocks a reaction of a proinflammatory factor with a receptor by emulsifying the proinflammatory factor.

The biological surfactant is at least one selected from cholic acid, chenodeoxycholic acid, deoxycholic acid, lithocholic acid, dehydrocholic acid, a conjugate thereof with glycine or taurine, or a pharmaceutically acceptable salt thereof.

The structural formulas of cholic acid, chenodeoxycholic acid, deoxycholic acid, lithocholic acid and dehydrocholic acid are as follows:

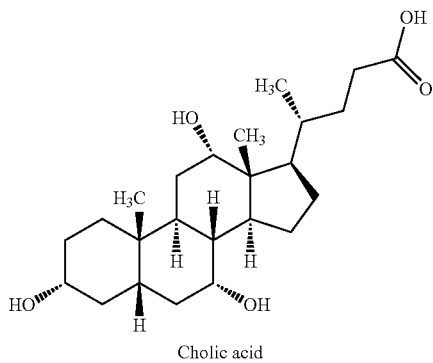

Cholic acid

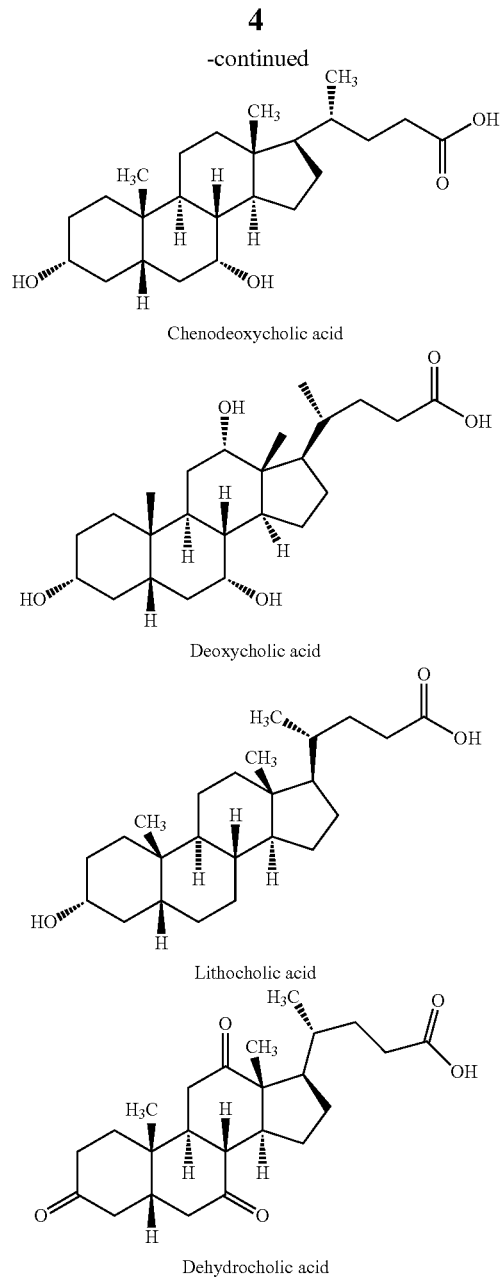

Chenodeoxycholic acid

Deoxycholic acid

Lithocholic acid

Dehydrocholic acid

The term "conjugate" in the context of the present invention refers to a compound that conjugates cholic acid, chenodeoxycholic acid, deoxycholic acid, lithocholic acid or dehydrocholic acid with glycine or taurine, for example glycocholic acid, taurocholic acid, glycochenodeoxycholic acid, taurochenodeoxycholic acid, glycodeoxycholic acid, taurodeocycholic acid, etc.

The term "pharmaceutically acceptable salt" in the context of the present invention refers to a compound that contains an ionic bond and may be produced by reacting the disclosed compound with either an acid or base, suitable for administering to a subject. For example, the "pharmaceutically acceptable salt" may be a sodium or potassium salt of cholic acid, chenodeoxycholic acid, deoxycholic acid, lithocholic acid, dehydrocholic acid, or a conjugation thereof with glycine or taurine.

The anti-inflammatory agent of the present invention blocks the interaction between a toxin or damaged tissue and a inflammatory cell, and inhibits the activation of the innate immune system thereby treating and preventing a inflammatory response caused by the toxin and damaged tissue. Also, the anti-inflammatory agent of the present invention may be used for the treatment and prevention of systemic inflammation.

The anti-inflammatory agent of the present invention may be used to block the reaction of a host cell with a bacterial toxin or an endogenous proinflammatory factor.

The anti-inflammatory agent may be used to treat or prevent an inflammation associated with a disease, such as Alzheimer's disease, arteriosclerosis, rheumatic arthritis, degenerative arthritis or protein misfolding disease, of which incidence or progression is caused by a proinflammatory substance of which hydrophobic region is excessively exposed.

Preferably, a dose of the anti-inflammatory agent of the present invention, which shows in vivo an anti-inflammatory effect without toxicity, is 0.1 mg/kg to 1 mg/kg.

Proinflammatory cytokine production and inflammatory cell activity which are stimulated by toxin can be inhibited when cell activation by toxin is blocked by the treatment with the anti-inflammatory agent of the present invention. The anti-inflammatory agent of the present invention shows no cytotoxicity with a concentration not exceeding 1 mg/ml. In a mouse test, no adverse effect was shown with the administration of sodium glycocholate at a dose of 250 mg/kg mouse, and the mortality of mice was significantly reduced with the administration of sodium glycocholate at a dose of 12.5 mg/kg mouse.

The administration route of anti-inflammatory agent of the present invention may be selected from oral, parenteral, injection, topical or rectal route. Also, the formulation of the anti-inflammatory agent of the present invention may be selected from a liquid solution, an ointment, a cream, a gel, a lotion, a suspension, a tablet, a capsule or a suppository.

It will be understood that the specific dose level for any particular patient will depend upon a variety of factors including the age, body weight, general health, sex, diet, time of administration, route of administration, rate of excretion, drug combination and the severity of the particular disease undergoing therapy.

Another object of the present invention can be achieved by providing an additive for tissue or cell preservative solution comprising at least one biological surfactant selected from cholic acid, chenodeoxycholic acid, deoxycholic acid, lithocholic acid, dehydrocholic acid, a conjugate thereof with glycine or taurine, or a pharmaceutically acceptable salt thereof.

When the additive for tissue or cell preservative solution of the present invention is added to the conventional organ preservative solution, an immune response induced by ischemia-reperfusion injury in the kidney is inhibited and the recovery of the kidney function is also aided. Therefore, the efficacy of an organ or cell preservative solution may be enhanced. In addition, the organ or cell preservative solution to which the additive for tissue or cell preservative solution of the present invention is added may be used for the purpose of treatment.

In the kidney test for rat damaged by ischemia-reperfusion injury, the enhancement of the kidney function and the inhibition effect of an inflammatory response were increased by the addition of the additive for tissue or cell preservative solution of the present invention. It is preferable to use the additive for tissue or cell preservative solution of the present invention in the range of 0.01 mg/ml to 10 mg/ml.

Yet another object of the present invention can be achieved by providing a therapeutic agent for sepsis, comprising a biological surfactant which blocks a reaction of a proinflammatory factor with a receptor.

The receptor may be a TGR5. TGR5 is a G protein-coupled receptor which is responsive to bile acids as a cell-surface receptor.

The biological surfactant may be a TGR5 agonist, and the TGR5 agonist may be at least one selected from cholic acid, chenodeoxycholic acid, deoxycholic acid, lithocholic acid, dehydrocholic acid, a conjugate thereof with glycine or taurine, or a pharmaceutically acceptable salt thereof.

ADVANTAGEOUS EFFECTS

The anti-inflammatory agent of the present invention inhibits effectively an inflammatory response caused by toxin or tissue damage. Also, when the additive for tissue or cell preservative solution of the present invention is added to an organ or cell preservative solution, the function of the organ or cell is enhanced. Moreover, the additive of the present invention may be used for a suppressive agent of various immune responses.

DESCRIPTION OF DRAWINGS

FIGS. 3A-3C show an inhibition efficacy of sodium glycocholate and sodium deoxycholate for the NF-κB activity of an E. coli LPS-stimulated CHO cell, in Example 2 of the present invention.

FIGS. 4A-4C show an inhibition efficacy of sodium glycochenodeoxycholate and sodium taurochenodeoxycholate for the NF-κB activity of an E. coli LPS-stimulated CHO cell, in Example 2 of the present invention.

FIGS. 30A-30C show cytotoxicity of chenodeoxycholic acid and glycocholic acid for a CHO cell in Example 10 of the present invention.

BEST MODE

Hereinafter, the present invention will be described in greater detail with reference to the following examples. The examples are given only for illustration of the present invention and not to be limiting the present invention.

EXAMPLE 1

Assay of the Inhibition for the Interaction Between Fluorescein-Labeled *E. coli* Lipopolysaccharide (LPS) and a Chinese Hamster Ovary (CHO) Cell Boron dipyrromethene difluoride (BODIPY), a fluorescein, labeled *E. coli* LPS and CHO cells were used. BODIPY-labeled LPS was reacted with sodium glycocholate in a glass tube at 37° C. for 14 hours. $2 \times 10^5$ CHO cells mixed with the reacting solution were plated per well in a 96-well plate, and then incubated at 37° C. for 14 hours. The incubated solution was stained with 7-amino-actinomycin D (7-AAD) and then analyzed by a flow cytometer. The analysis was performed at least twice per each treatment group and the obtained data were statistically processed by t-test. The result was $P<0.05$ in comparison with the experimental group in which CHO cells were treated with only BODIPY-LPS.

Figure 1:
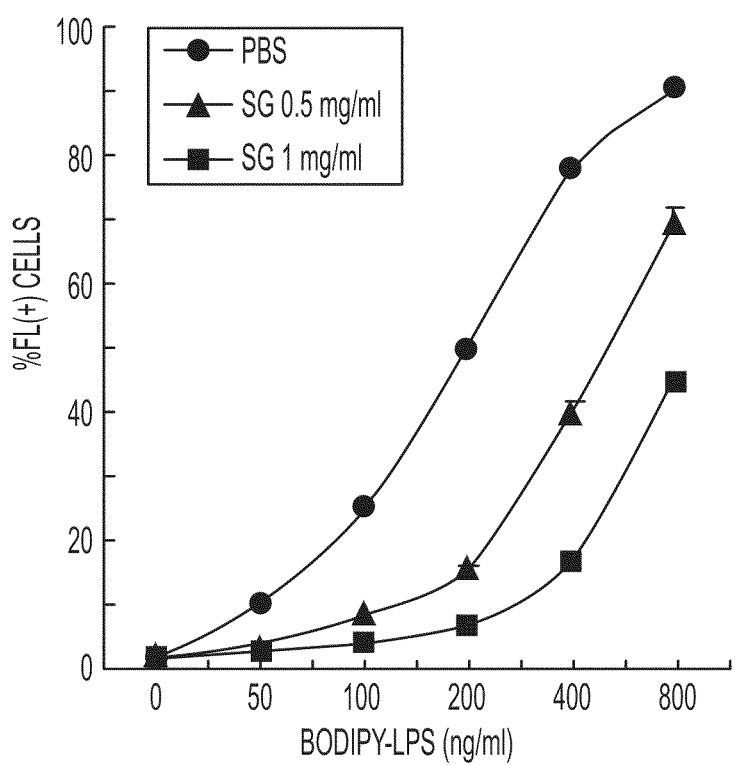
FIG. 1 shows an inhibition efficacy of sodium glycocholate for the interaction between fluorescein-labeled *E. coli* LPS and a CHO cell, in Example 1 of the present invention.

7-AAD(−) cells were selected in order to analyze living cells. As shown in FIG. 1, it was confirmed that the amount of fluorescence of BODIPY increased as the concentration of BODIPY-LPS increased. Also, the interaction between BODIPY-LPS and the cell was inhibited according to the increase of the concentration of sodium glycocholate, and such inhibition efficacy was decreased with the increase of the concentration of BODIPY-LPS (FIG. 1). Therefore, it could be realized that Inflammatory inhibition efficacy of sodium glycocholate shown in the LPS-stimulated inflammatory response was due to the blocking of the interaction between LPS and cells by the action of sodium glycocholate.

EXAMPLE 2

Assay of the Inhibition for the Activation of *E. Coli* LPS-Stimulated NF-κB

In order to evaluate the inhibition efficacy for the activation of *E. coli* LPS-stimulated NF-κB in a CHO cell, % expression of CD 25 in the CHO cell was evaluated as the following method, and FACS analysis after staining with 7-AAD was carried out to evaluate the cytotoxicity. Bile salts were classified into 3 groups based on their solubility in different solvents, as follows:

Group I. Water-soluble chemicals: sodium glycocholate hydrate, sodium deoxycholate, sodium glycochenodeoxycholate, sodium taurochenodeoxycholate, sodium taurocholate hydrate, sodium taurodeoxycholate hydrate

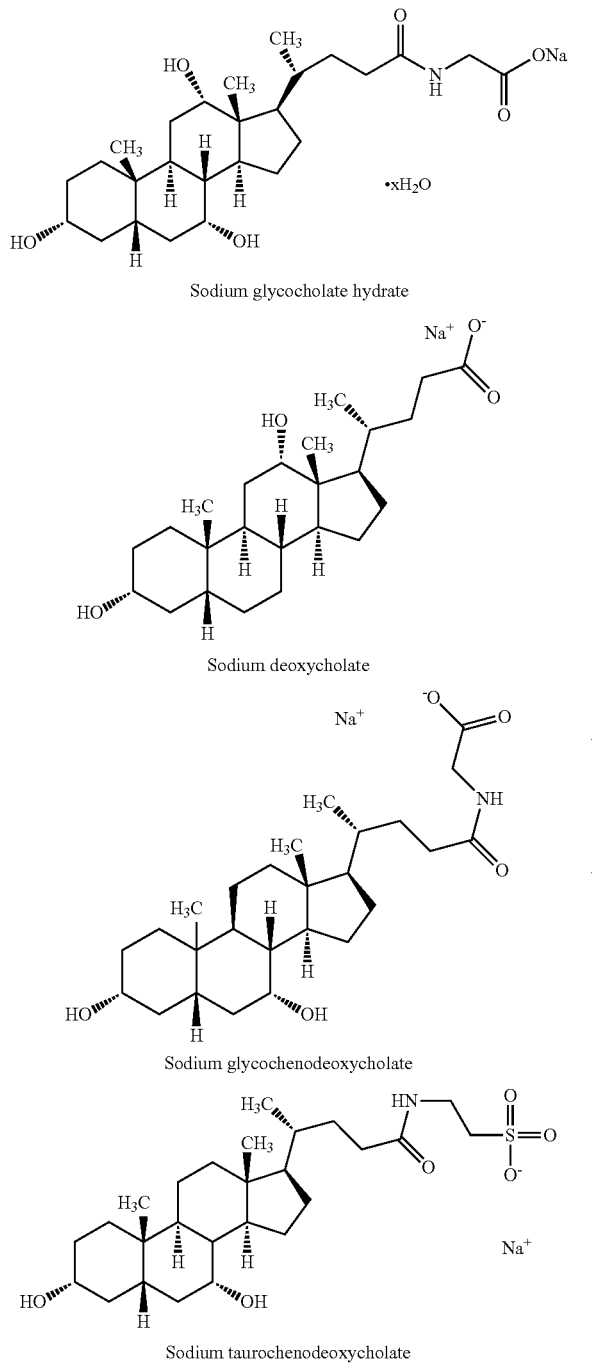

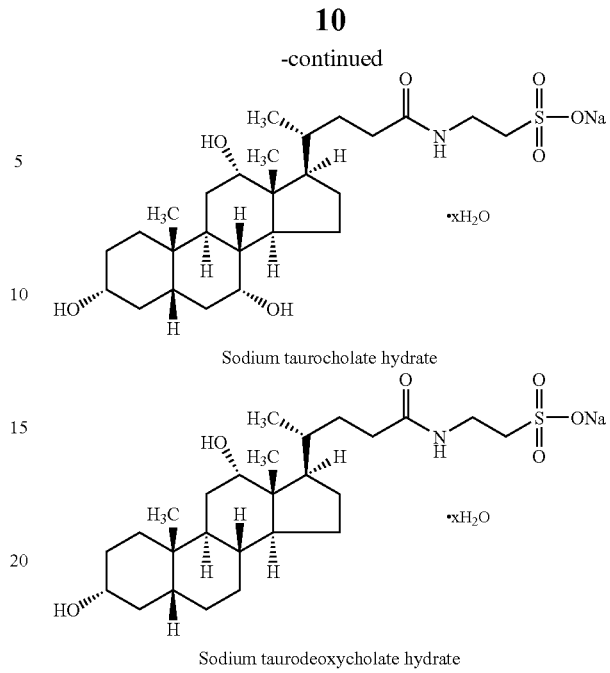

Figure 2A:
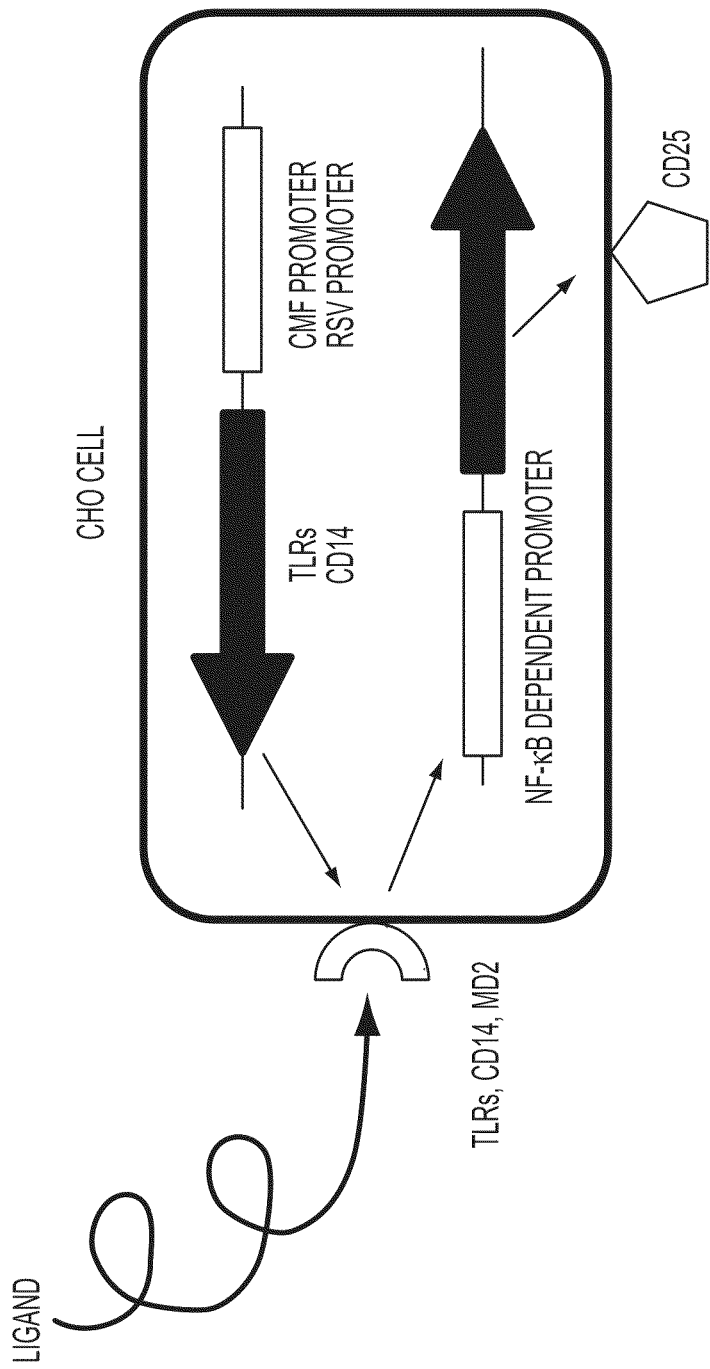
FIG. 2A shows a CHO cell system which expresses CD25 under the regulation of a nuclear factor (NF-κB) promoter.
Figure 2B:
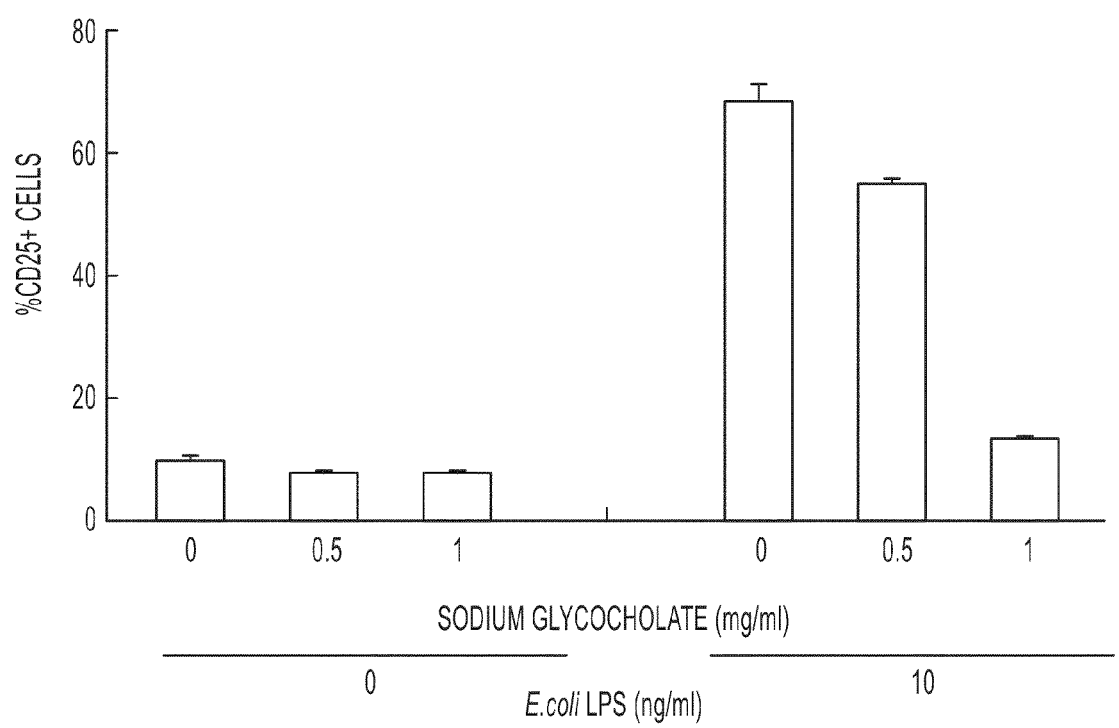
FIG. 2B shows an inhibition efficacy of sodium glycocholate for the activity of an *E. coli* LPS-stimulated CHO cell, in Example 1 of the present invention. % CD25+ cell means a fraction of NF-κB activated cells.
Figure 3C:
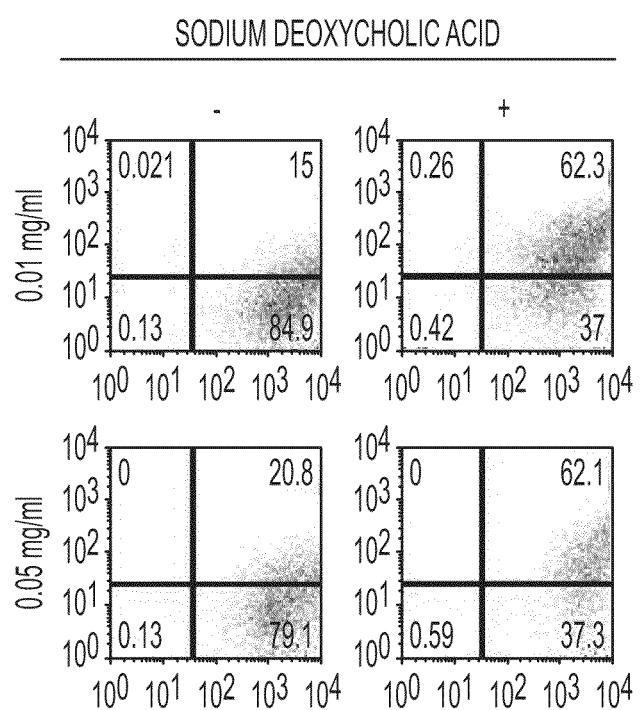
Figure 4C:
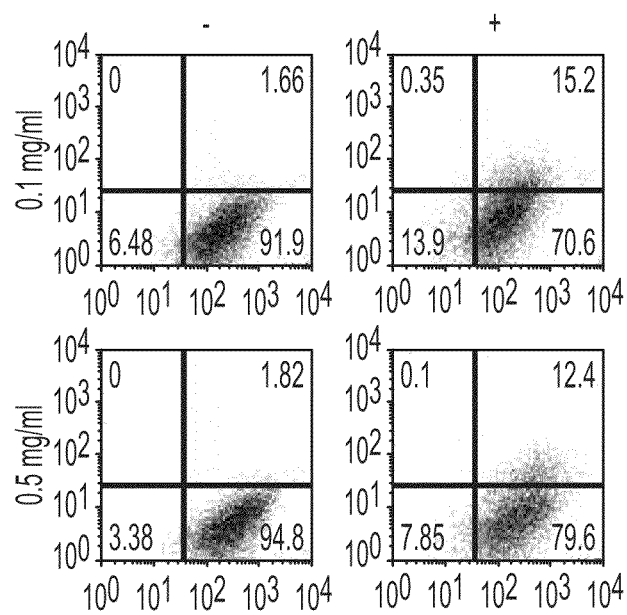
Figures 5A, 5B:
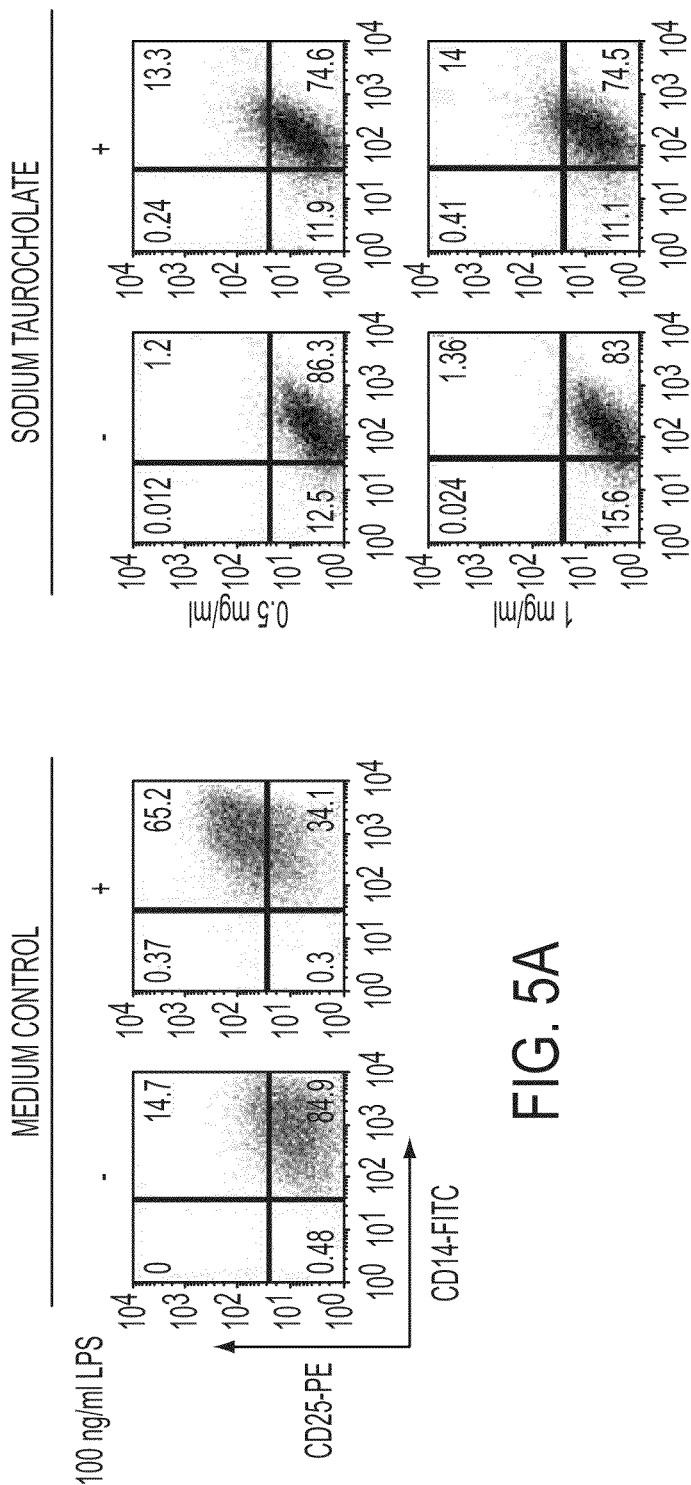
FIGS. 5A-5C show an inhibition efficacy of sodium taurocholate and sodium taurodeoxycholate for the NF-κB activity of an E. coli LPS-stimulated CHO cell, in Example 2 of the present invention.
Figure 5C:
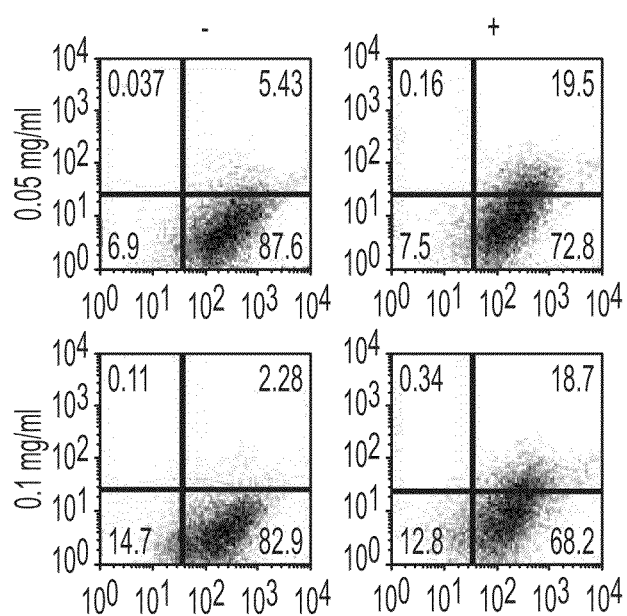
Figures 6A, 6B:
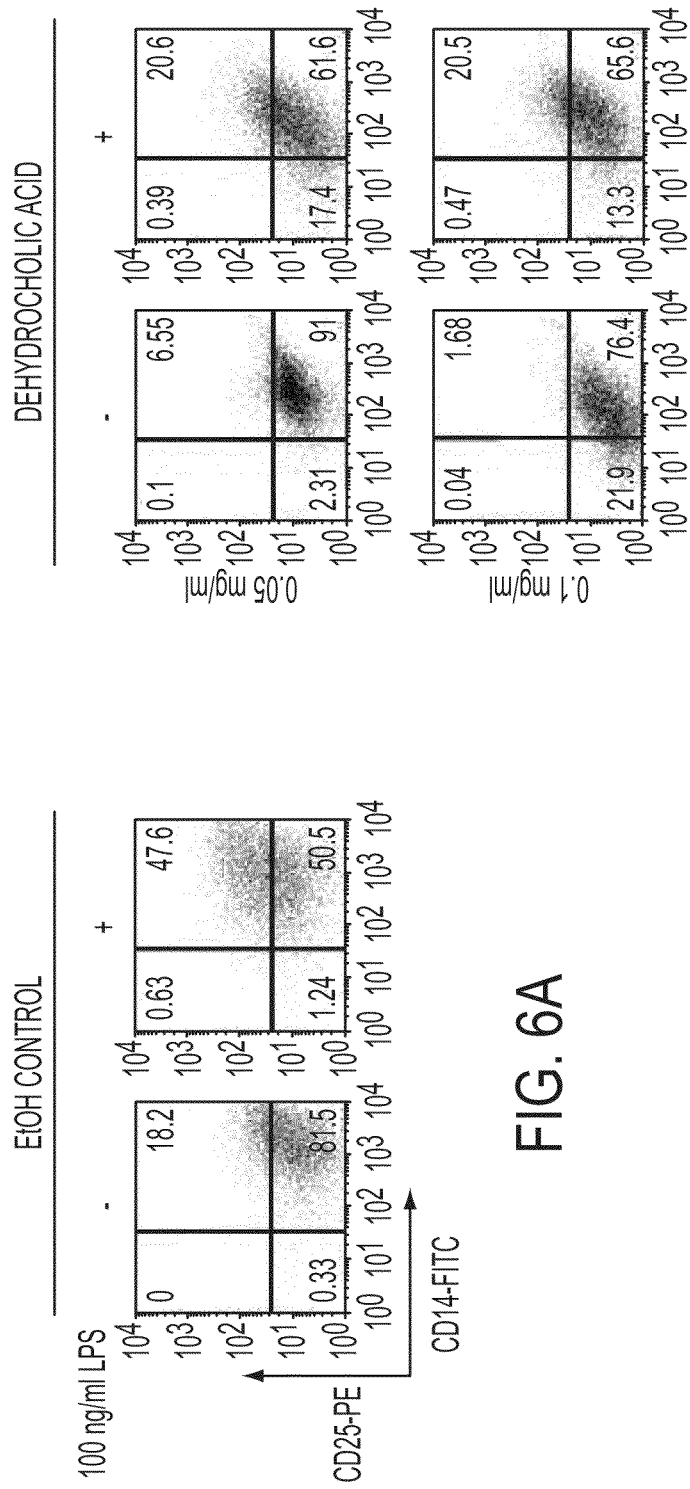
FIGS. 6A-6C show an inhibition efficacy of dehydrocholic acid and lithocholic acid for the NF-κB activity of an E. coli LPS-stimulated CHO cell, in Example 2 of the present invention.
Figure 6C:
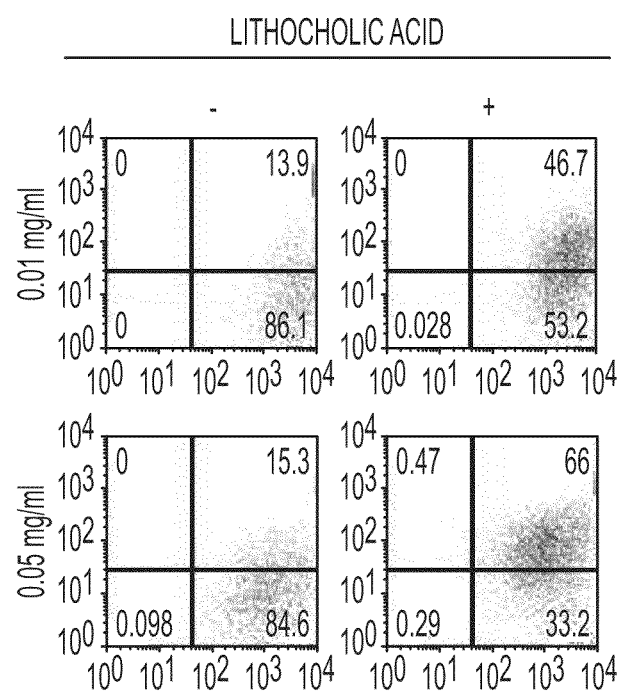
Figures 7A, 7B:
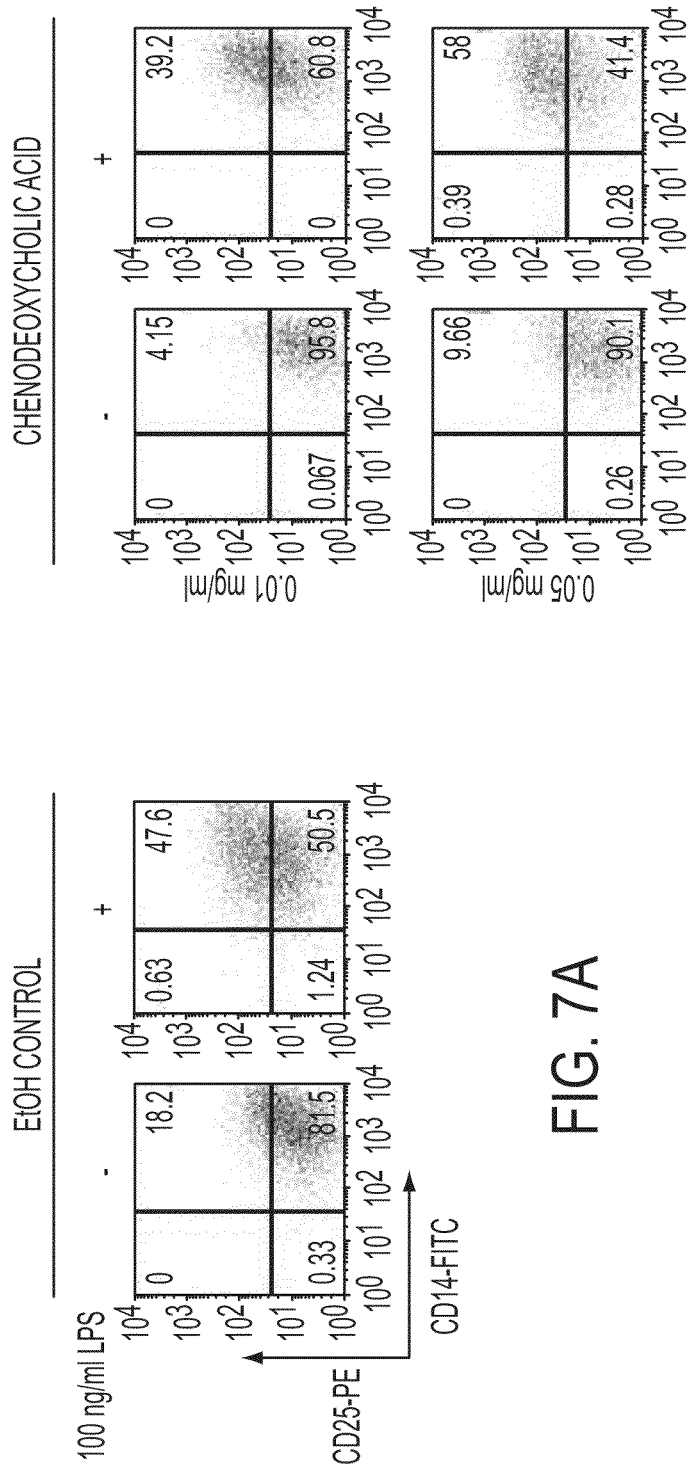
FIGS. 7A-7C show an inhibition efficacy of chenodeoxycholic acid and glycocholic acid hydrate for the NF-κB activity of an E. coli LPS-stimulated CHO cell, in Example 2 of the present invention.
Figure 7C:
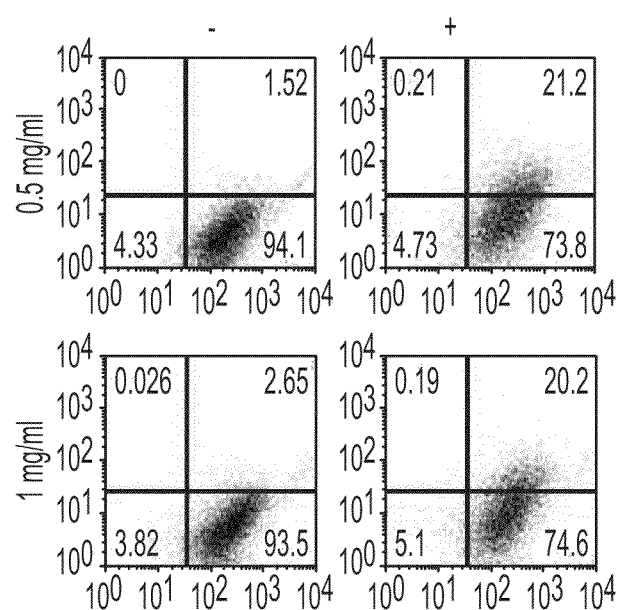

Group II. Ethanol-soluble chemicals: dehydrocholic acid, lithocholic acid, chenodeoxycholic acid, glycocholic acid hydrate Group III. Methanol-soluble chemical: cholic acid Culture and Stimulation of Cells The CHO cells expressing CD25 under the regulation of a nuclear factor (NF-κB) promoter, shown FIG. 2A, were used for this experiment. Toll-like receptor 2 (TLR2) and CD14 gene-transformed CHO cells (hereinafter referred to as "3FP cells") were also used.

3FP cells which were selectively cultured with Ham's F-12 basal medium (containing 5% FBS, 0.584 g/l L-glutamine, Penicillin-streptomycine, 400 μg/ml hygromycin, 50 μg/ml G418, and 50 μg/ml gentamycin) were separated from the culture solution with Trypsin-DETA, and were seeded at $3 \times 10^5$ cells/well in a 96-well plate, and then cultured for 18 hr. The next day, the cultured cells were treated with bile acid derivatives and LPS, and were incubated in a $CO_2$ incubator for 15 hr at 37° C.

Flow Cytometry Experiment

After stimulating the above incubated cells for 15 hr, the culture solution was centrifuged (1200 rpm, 5 min, 4° C.) to remove the culture supernatant. The precipitate was washed twice with 200 μl of FACS buffer (1×PBS containing 1% BSA and 1 mM EDTA). 20 μl of blocking solution (PBS containing 1:10 of normal mouse serum and 1:3 of anti-human CD14/CD32 (BD, 2.4G2) was added to each well and reacted on an ice for 30 min. A mixture solution of anti-human CD25-PE (1:16) and anti-human CD14-FITC (1:32) was added to the well and then reacted on the ice for 30 min. The reaction mixture was washed twice with 200 μl of FACS buffer, and then 200 μl of 7-AAD (1:20) was added to the reaction mixture. After the reaction mixture was reacted on the ice for 10 min, CD25 expression efficacy and cytotoxicity were analyzed by using a flow cytometer.

Evaluation of the Influence of Bile Salts for LPS-Stimulated CD25 Expression Efficacy 1) Group I. Water-Soluble Chemicals According to the investigation results of CD25 expression of live 7AAD(−) LPS-stimulated 3FP cells, sudium glycochenodeoxycholate, sodium taurochenodeoxycholate, sodium taurocholate hydrate, sodium taurodeoxycholate hydrate, sodium deoxycholate besides sodium glycocholate hydrate out of the bile acid derivatives showed an inhibition effect for LPS-stimulated CD25 expression (NF-κB activation) (FIG. 2B and FIGS. 3A-3C to FIG. 8).

In order to analyze living cells, 7-AAD(-) cells were selected and an activation of nuclear transcription factor was confirmed by the increase of CD25 expression. As shown FIG. 2B, the nuclear transcription factor activation of 3FP cells by LPS was inhibited depending on the concentration of sodium glycocholate. The nuclear transcription factor was inhibited as to be 21.7±0.9% ($p<0.05$) under the presence of 0.5 mg/ml of sodium glycocholate, and as to be 88.2±1.2% ($p<0.05$) under the presence of 1 mg/ml of sodium glycocholate.

2) Group II. Ethanol-Soluble Chemicals

According to the investigation results of CD25 expression of live&AAD(-)LPS-stimulated 3 FP cells, dehydrocholic acid, glycocholic acid hydrate, lithocholic acid and chenodeoxycholic acid among the bile acid derivatives showed inhibition effects on the expression of CD25 (NF-κB activation) (FIGS. 6A-6C and FIGS. 7A-7C).

3) Group III. Methanol-Soluble Chemical

Figure 8:
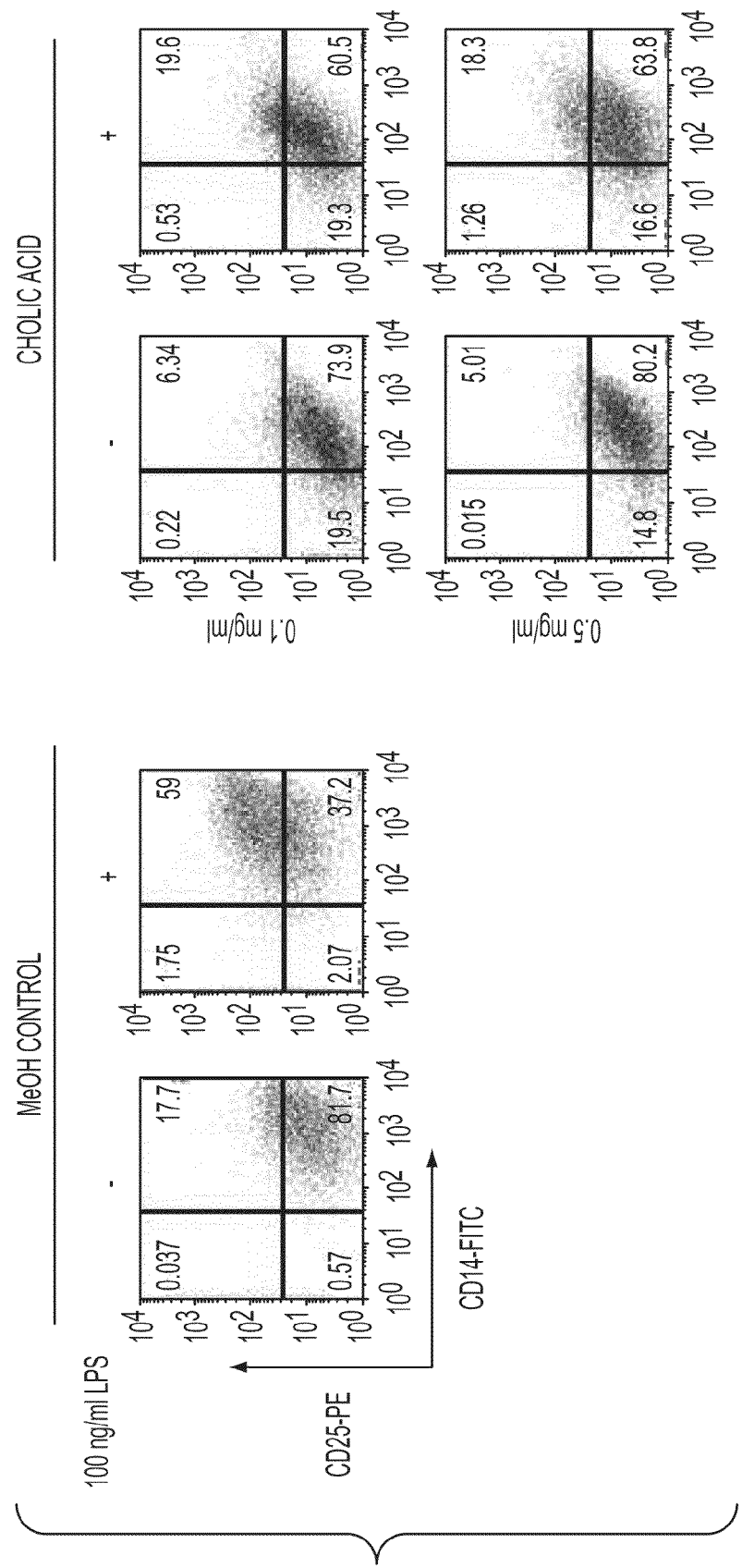
FIG. 8 shows an inhibition efficacy of cholic acid for the NF-κB activity of an *E. coli* LPS-stimulated CHO cell, in Example 2 of the present invention.
Figure 9A:
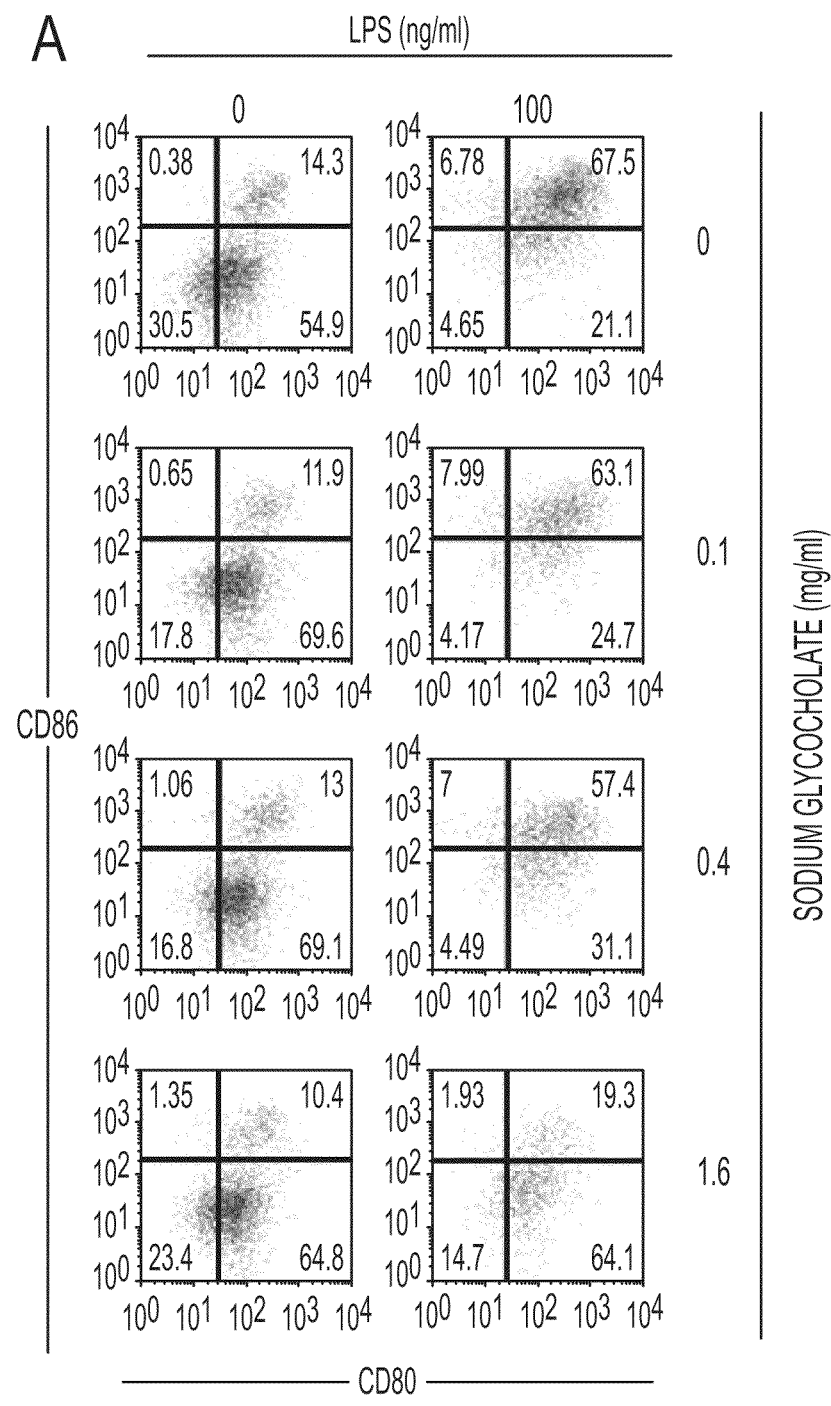
FIGS. 9A-9B show an inhibition efficacy of sodium glycocholate for the activity of an E. coli LPS-stimulated dendritic cell, in Example 3 of the present invention.
Figure 9B:
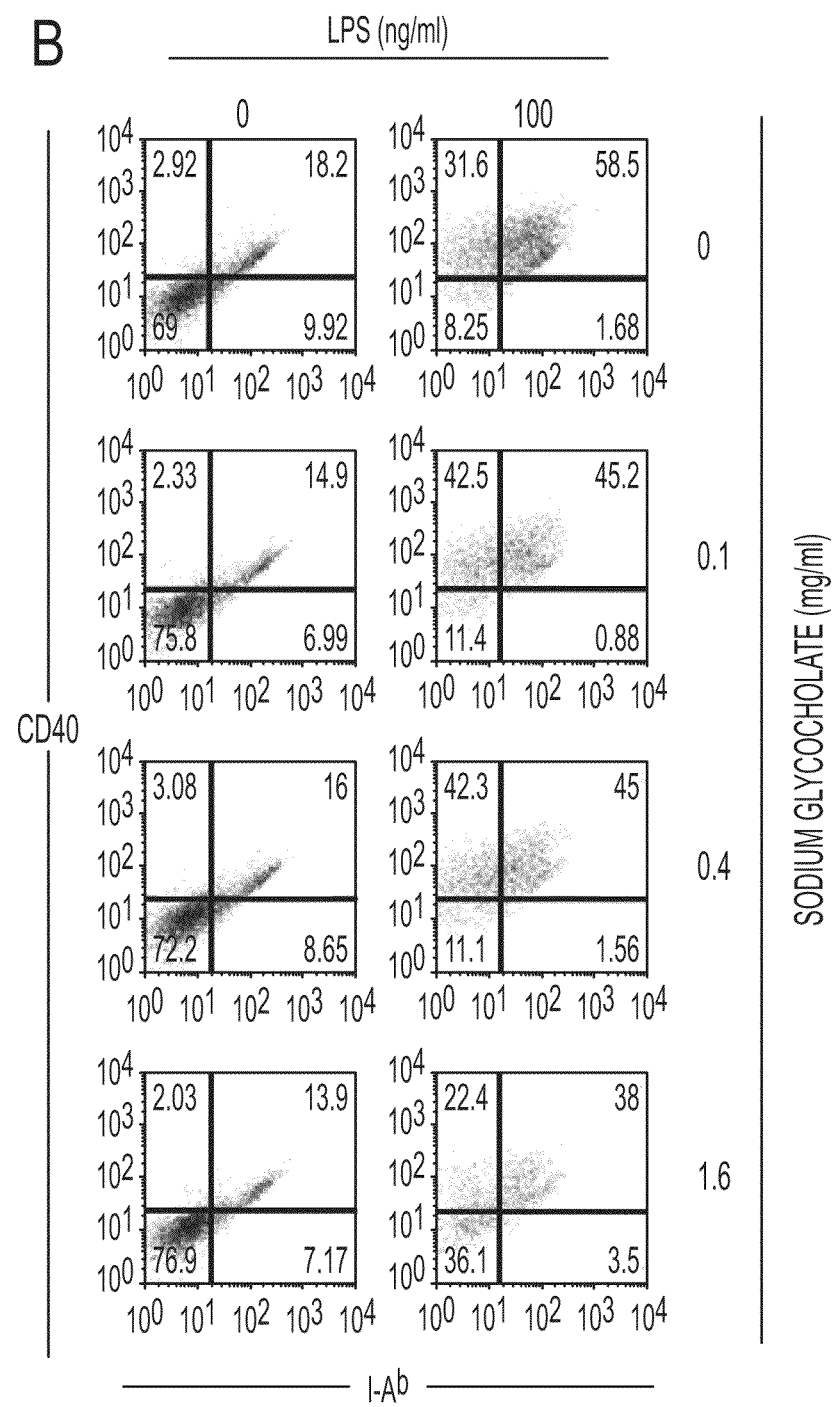
Figure 10A:
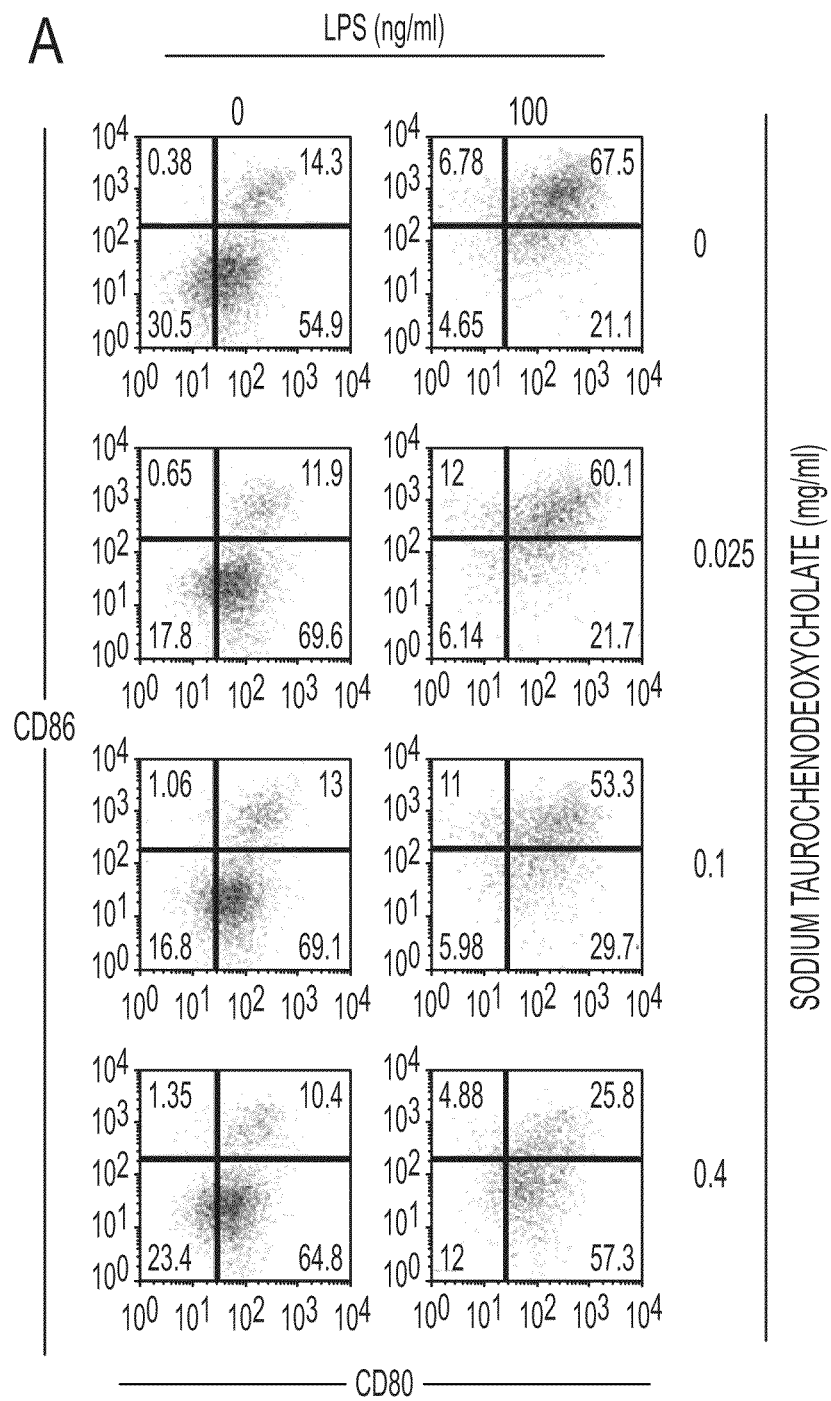
FIGS. 10A-10B show an inhibition efficacy of sodium taurochenodeoxycholate for the activity of an E. coli LPS-stimulated dendritic cell, in Example 3 of the present invention.
Figure 10B:
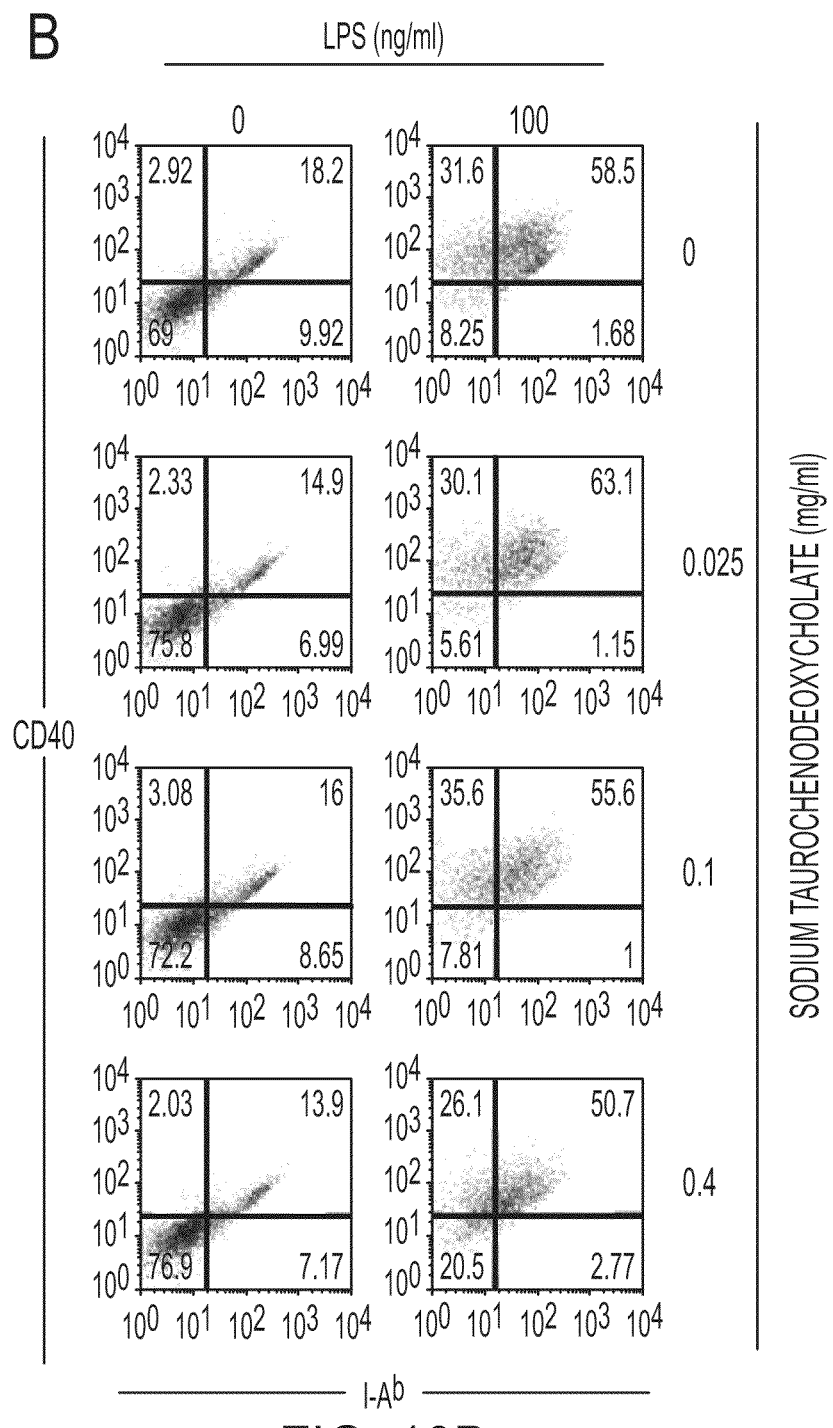
Figure 11A:
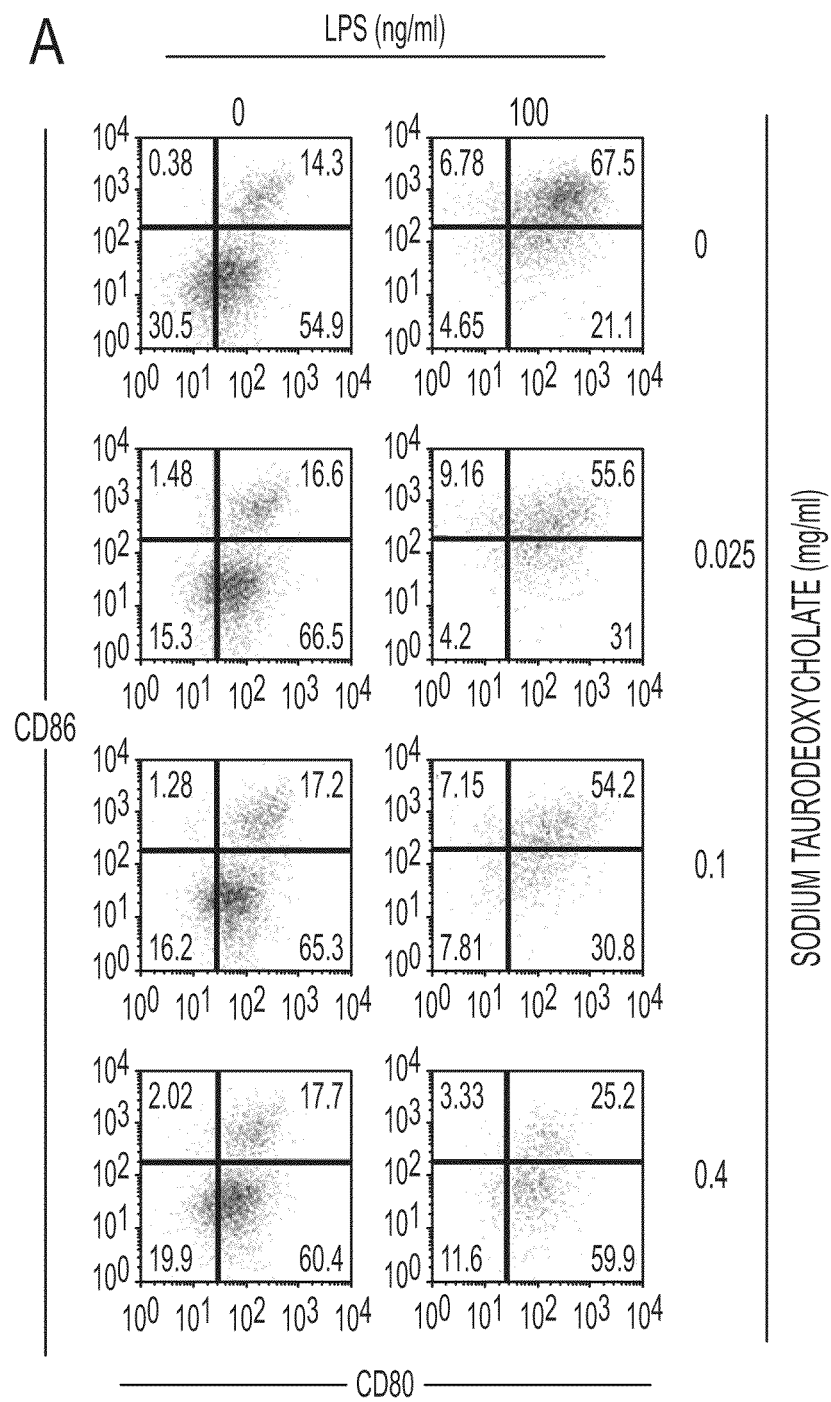
FIGS. 11A-11B show an inhibition efficacy of sodium taurodeoxycholate for the activity of an E. coli LPS-stimulated dendritic cell, in Example 3 of the present invention.
Figure 11B:
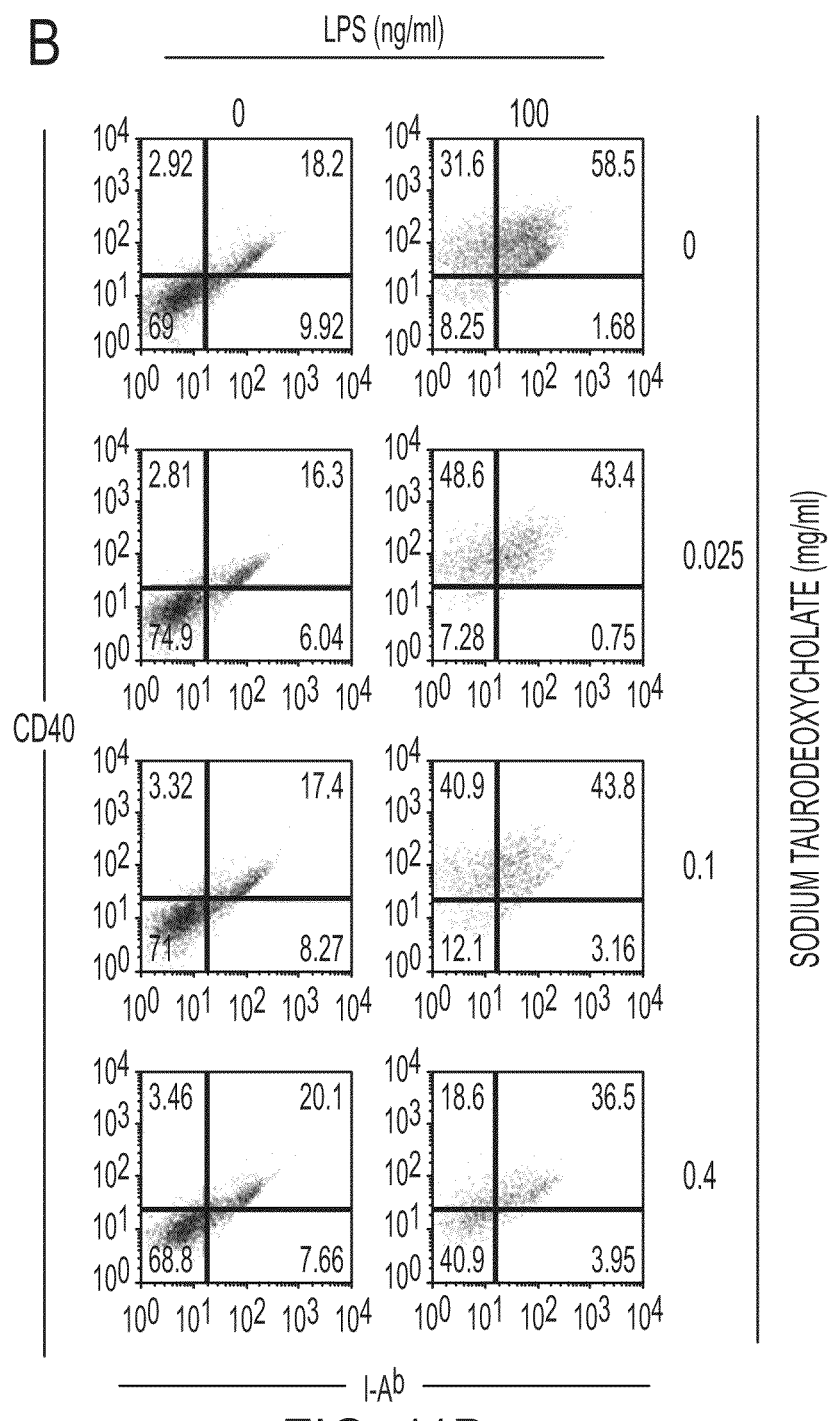

According to the investigation results of CD25 expression of live 7AAD(-) LPS-stimulated 3FP cells, cholic acid, among the bile acid derivatives, dissolved in methanol showed inhibition effects (FIG. 8).

EXAMPLE 3

Assay of the Inhibition of Sodium Glycocholate on LPS which Activates Dendritic Cells In order to assay the effect of sodium glycocholate on the activation procedure of antigen presenting cells, which is induced by *E. coli* LPS, cells were separated from the bone marrow of recombination activating gene 2 (Rag2) deficient mouse. The separated cells were plated at $2\times10^5$ cells/well in a 96-well plate and then treated with 1.5 ng/ml of granulocytmacrophage colony-stimulating factor (GM-CSF) and 0.75 ng/ml of interleukin-4 followed by the differentiation of the cells into dentritic cells through 6-day incubation.

The dendritic cells were well mixed with sodium glycocholate and LPS. The mixtures were stimulated for 18 hours at 37° C., and stained with anti-CD40-FITC, anti-CD80-FITC, anti-I-Ab-PE, anti-CD86-PE, 7AAD and anti-CD11c-APC, then the cells were assayed via a flow cytometer. Each group was treated and assayed at least twice, and the results were statistically analyzed through t-test. The results were $p<0.05$ compared with the experimental groups treated by only LPS.

As shown FIGS. 9A-9B to 11A-11B, in order to assay only living dedritic cells, CD11c(+)/7AAD(-) cells were selected and then the expressions of dendritic cell costimulatory molecules and I-Ab were assayed. The increased expression of CD40, CD80, CD86 and I-Ab by 100 ng/ml of *E. coli* LPS was inhibited depending on the concentration of sodium glycocholate, and also was inhibited depending on the concentration of sodium taurochenodeoxycholate and sodium taurodeoxycholate hydrate. Consequently, it was shown that dentritic cells were significantly inhibited by LPS.

EXAMPLE 4

Assay of In Vitro Proinflammatory Cytokine Generation by *E. coli* LPS

In order to assay the effect of sodium glycocholate on the generation of proinflammatory cytokines induced by *E. coli* LPS, dendritic cells were prepared in the same way as Example 3, and macrophages were separated from the abdomen of C57BL/6 mouse. Thereafter, sodium glycocholate and LPS were reacted in vitro for 1 hour at 37° C., and then mixed with the cells. Each cell was stimulated for 14 hours at 37° C., and then supernatant fluid was separated.

The concentrations of TNF-α and interleukin-12p40 in the separated supernatant fluid was measured by an enzyme-linked immunoabsorbent assay (ELISA).

Figure 12:
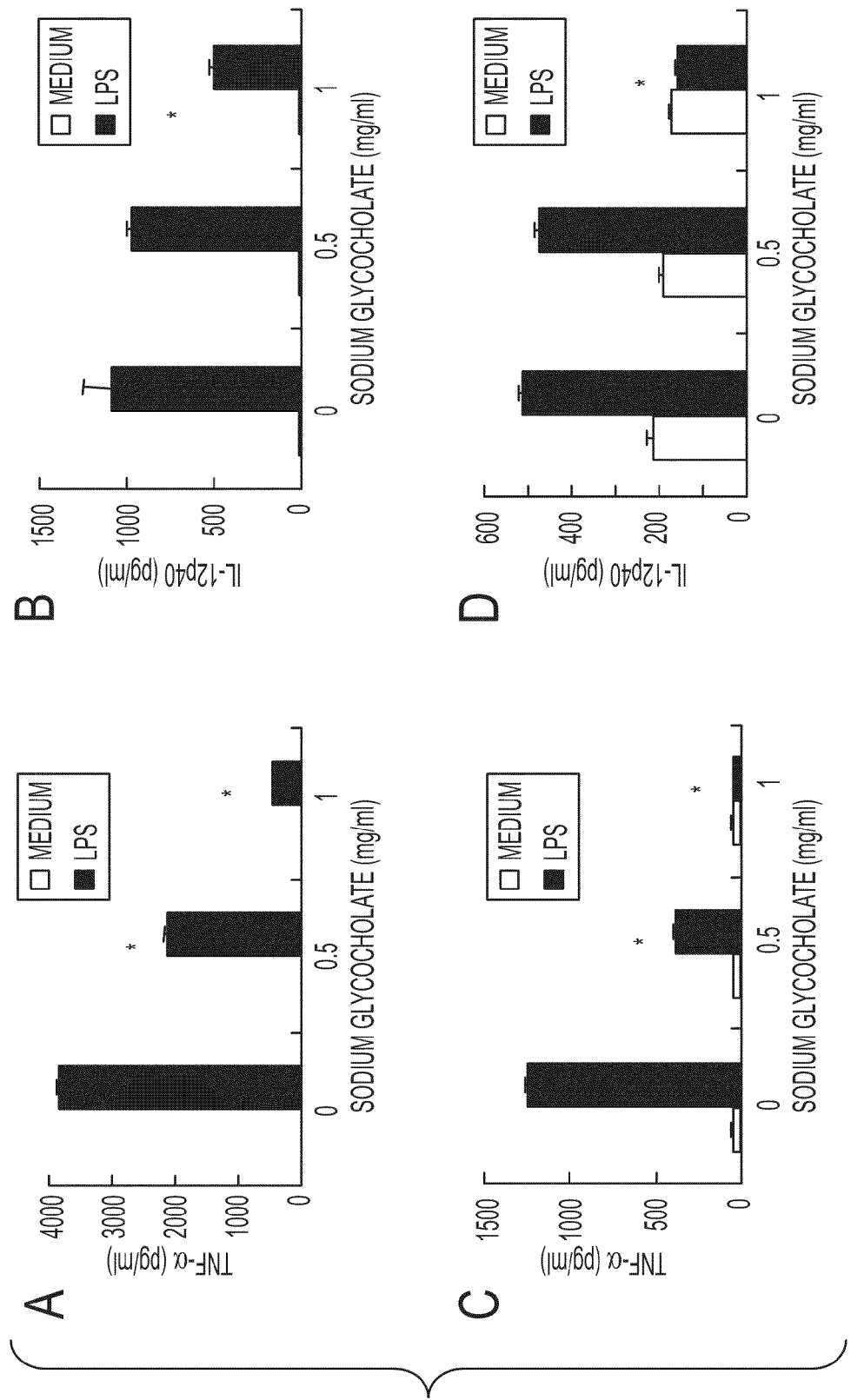
FIG. 12 shows an efficacy of sodium glycocholate for the proinflammatory cytokine production of an *E. coli* LPS-stimulated mouse abdominal (A, B) and dendritic (C, D) cell, in Example 4 of the present invention.

The generation of TNF-α from the macrophages and the dendritic cells by the LPS stimulation were inhibited so as to be 42.2±0.9% ($p<0.05$) and 70.2±2.3% ($p<0.05$) respectively at 0.5 mg/ml of sodium glycocholate, and 87.8±0.2% ($p<0.05$) and 101.0±0.2% ($p<0.05$) respectively at 1 mg/ml of sodium glycocholate. It was also shown that, in the generation of interleukine-12p40 by LPS, the macrophages and the dendritic cells were inhibited so as to be 9.8±11.0% ($p<0.05$) and 4.7±3.1% ($p<0.05$) respectively at 0.5 mg/ml of sodium glycocholate, and 54.3±4.1% ($p<0.05$) and 106.6±1.3% ($p<0.05$) respectively at 1 mg/ml of sodium glycocholate (FIG. 12).

Each group was treated and assayed at least twice, and the results were statistically analyzed through t-test. The results were $p<0.05$ compared with the experimental groups treated by only LPS.

EXAMPLE 5

Assay of the Inhibition of the Generation of Nitric Oxide (NO) in Dendritic Cells and Macrophages by *E. coli* LPS In order to assay the effect of sodium glycocholate on the generation of NO, a cytotoxic factor, induced by LPS, dendritic cells were prepared in the same way as Example 4. The dendritic cells were treated with sodium glycocholate, sodium taurochenodeoxycholate and sodium taurodeoxycholate hydrate, respectively, and then stimulated with LPS for 18 hours at 37° C. Then, the resulting dendritic cell mixtures were plated, by 100 ml each, in a 96-well plate. Griss reagents were added to each well, and the 96-well plate was covered with foils and kept reacting for 15 min at room temperature. Absorbance at 540 nm was measured using an ELISA reader. Macrophages separated from abdomen were also treated with sodium glycocholate, sodium taurochenodeoxycholate and sodium taurodeoxycholate, respectively, and then stimulated with LPS for 18 hours. Thereafter, the same experiments as the dentritic cells were performed to the macrophages.

Figure 13:
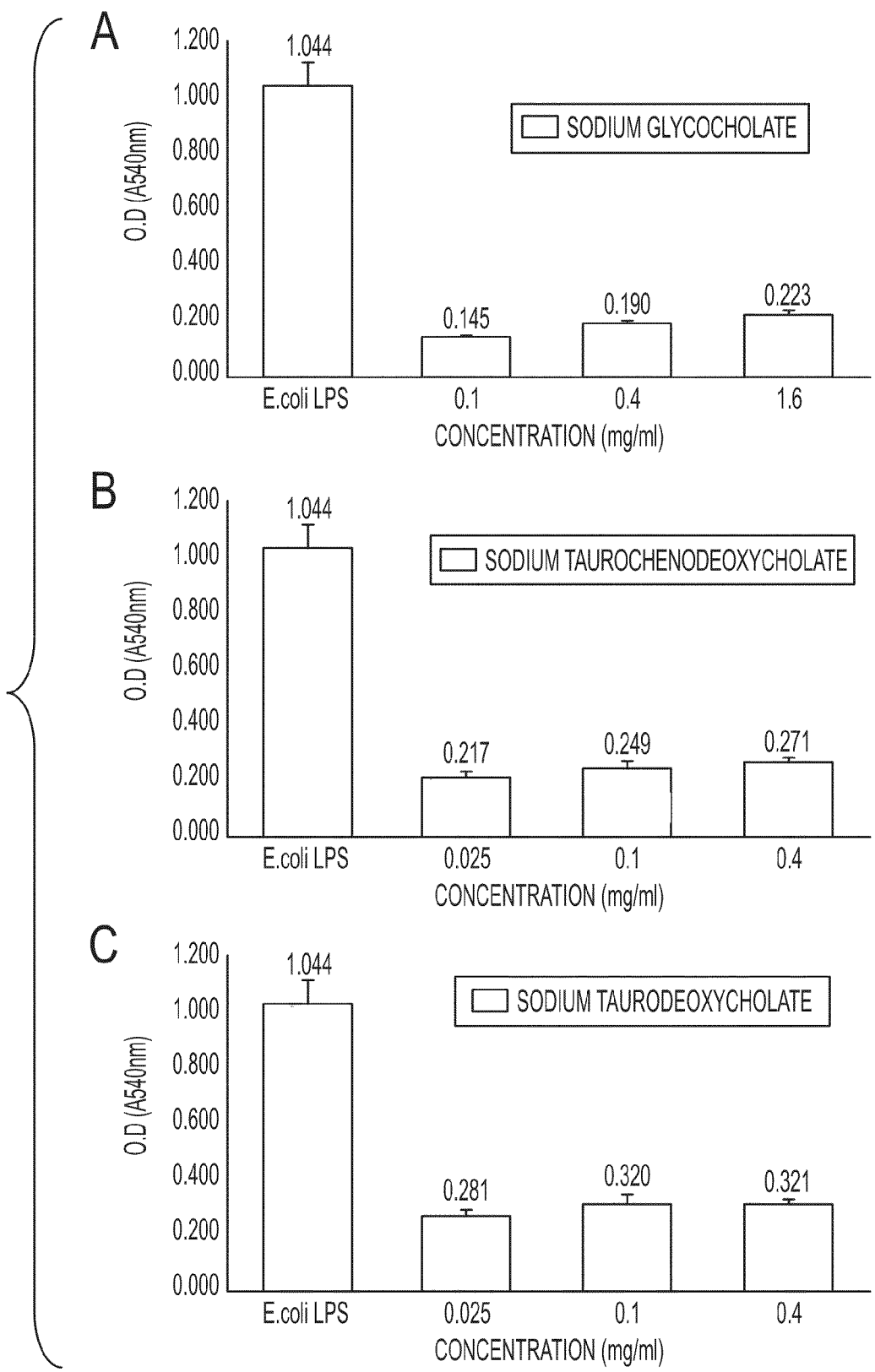
FIG. 13 shows an efficacy of sodium glycocholate, sodium taurochenodeoxycholate and sodium taurodeoxycholate for the nitric oxide (NO) production of an *E. coli* LPS-stimulated abdominal cell, in Example 5 of the present invention.
Figure 14:
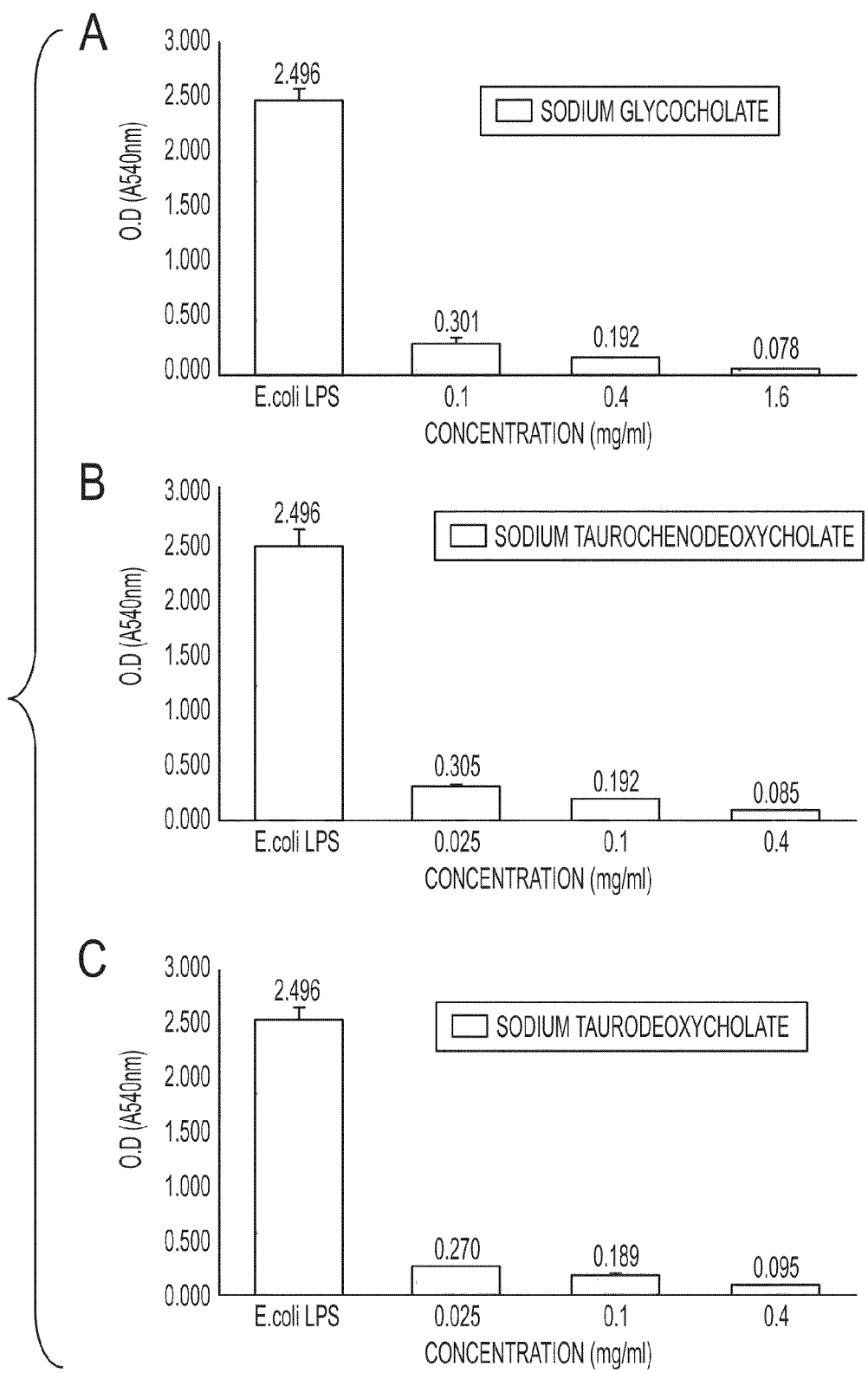
FIG. 14 shows an efficacy of sodium glycocholate, sodium taurochenodeoxycholate and sodium taurodeoxycholate for the NO production of an *E. coli* LPS-stimulated macrophage, in Example 5 of the present invention.

As shown in FIG. 13A and FIG. 14A, the generation of NO by the macrophages and dendritic cells stimulated by LPS was inhibited by sodium glycocholate. The generation of NO by the macrophages and dendritic cells stimulated by LPS was also inhibited by sodium taurochenodeoxycholate and sodium taurodeoxycholate hydrate, as shown in FIG. 13B, FIG. 13C, FIG. 14B and FIG. 14C. Considering these results, it could be understood that the above 3 bile acid derivatives inhibit the generation of NO which plays an important role in the progression of inflammation.

EXAMPLE 6

Assay of Inhibition of the Activation of Dendritic Cell-Mediated T Cell by *E. coli* LPS Antigen presenting cells activated by LPS activates T cells. It was tested whether dendritic cells blocked by sodium glycocholate can activate T cells when LPS activates dendritic cells. Cells were harvested from the bone marrow of Rag2 deficient male mouse. The harvested cells were plated at $4 \times 10^3$ cells/well in a 96-well plate and treated with 1.5 ng/ml of granulocyte colony-stimulating factors and 0.75 ng/ml of interleukin-4, and then incubated for 6 days to differentiate into dendritic cells. Sodium glycocholate was reacted with LPS for 1 hour at 37° C., and then mixed with the dendritic cells. The dendritic cells were stimulated for 14 hours at 37° C., and CD3+ and CD4+ T cells separated from female Marilyn mouse having H-Y antigen-specific T cell receptor (TCR), were incubated with the dendritic cells for 72 hours. [3H]-methylthymidine was added, at 1 µCi/well, to the 96-well plate and then incubated for 18 hours. Cells were harvested from the 96-well plated and then CPM (count per minute) was measured through a beta counter.

Figure 15:
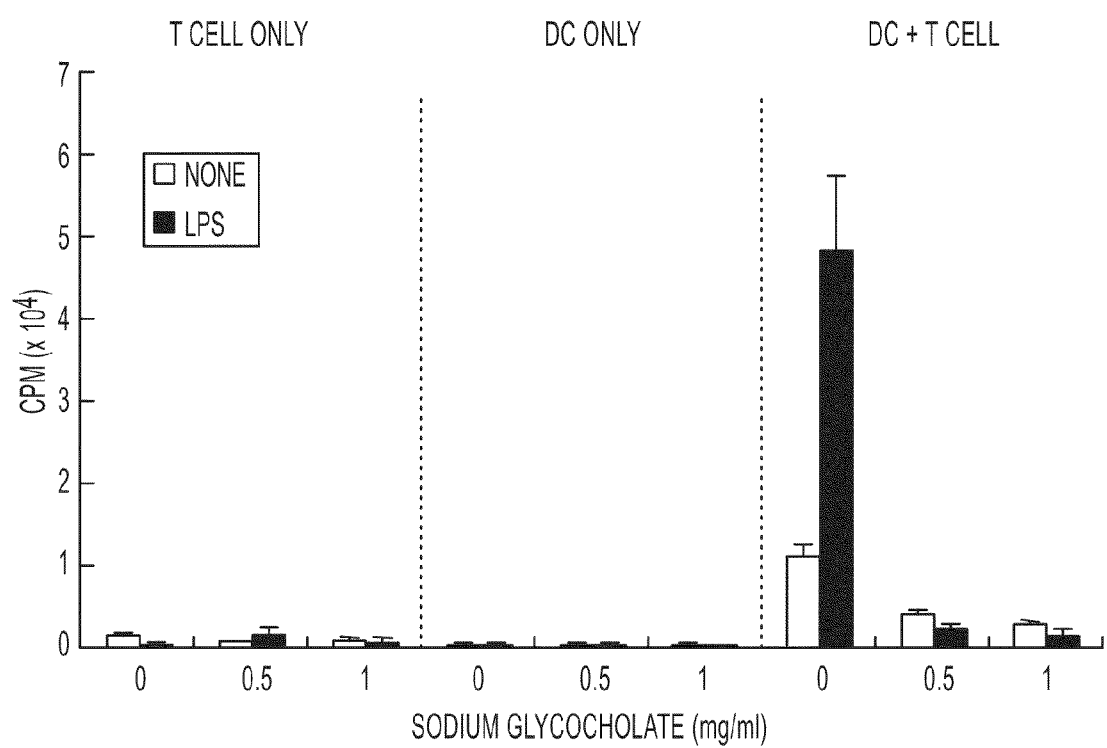
FIG. 15 shows an efficacy of sodium glycocholate for the T cell activity by an *E. coli* LPS-stimulated dendritic cell, in Example 6 of the present invention.

The proliferation of dendritic cell-mediated T cell was inhibited so as to be 104.9±3.2% (p<0.05) at 0.5 mg/ml of sodium glycocholate, and 105.1±3.2% (p<0.05) at 1 mg/ml of sodium glycocholate (FIG. 15). T cell proliferation by LPS or sodium glycocholate was not observed in experimental groups in which only dendritic cells or T cells were incubated. Consequently, it was understood that the activity of dendritic cells induced by LPS and thus the activity of dendritic cell-mediated T cells was inhibited (p<0.05).

EXAMPLE 7

Assay of the Protection of Sodium Glycocholate in LPS Mouse Model of Sepsis

Figure 16:
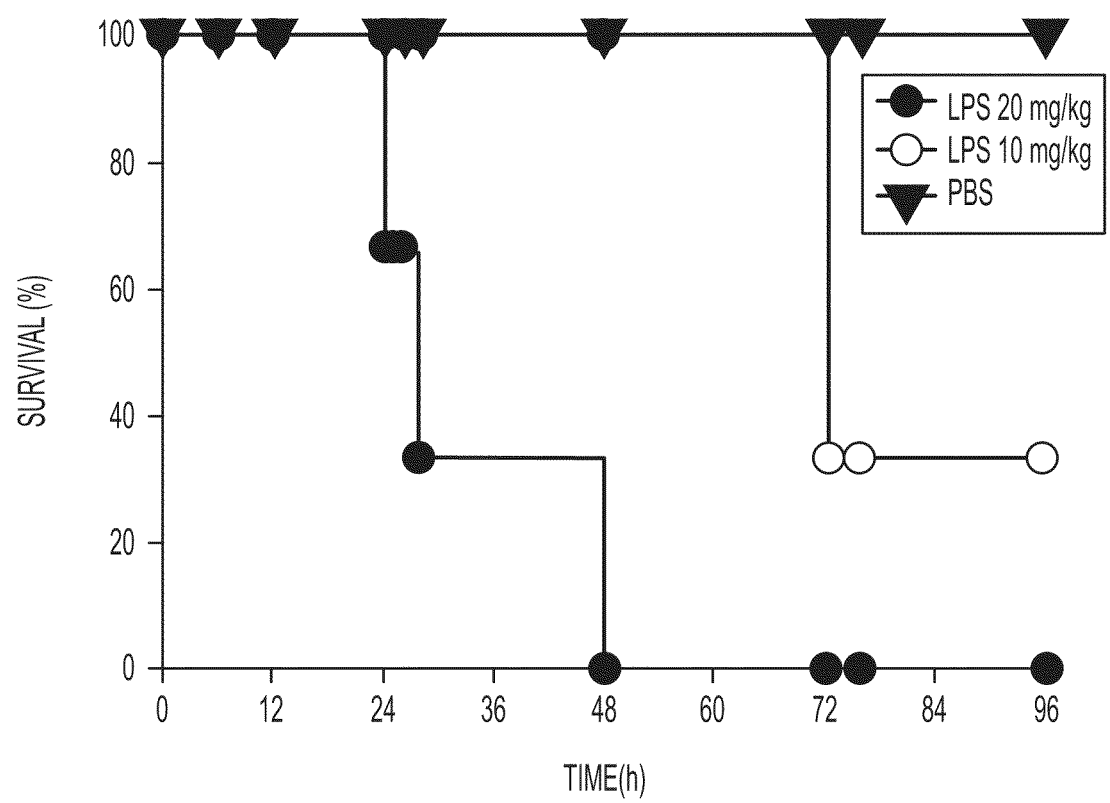
FIG. 16 is a graph relating to the determination of the concentration of LPS to be administered to a C57BL/6 mouse, in Example 7 of the present invention.

In order to assay the neutralizing capacity of sodium glycocholate to LPS, three C57BL/6 mice of 6 weeks age were used per each group. 20 mg/kg and 10 mg/kg of LPS were administered into abdomen of the mouse in order to measure $LD_{50}$ of LPS. It was observed that 20 mg/kg of LPS is the best optimal concentration for the test of protection test (FIG. 16).

Figure 17:
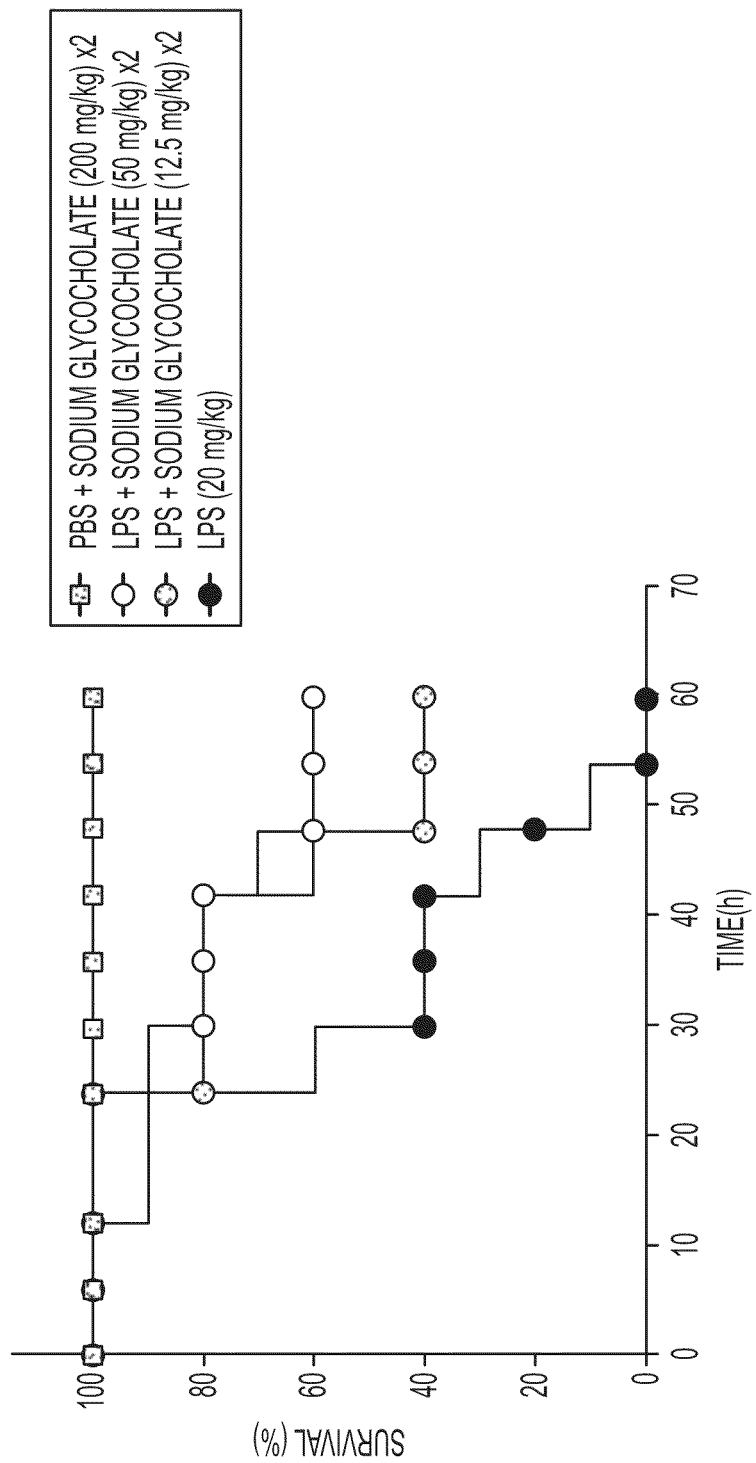
FIG. 17 shows an efficacy of sodium glycocholate for the survival rate of LPS-administered C57BL/6 mice, in Example 7 of the present invention.

The in vitro neutralizing capacity of sodium glycocholate to LPS was assayed. The survival rate was measured after 20 mg/kg of LPS was administered into the abdomen of mice and then 12.5 mg/kg of sodium glycocholate, and 20 mg/kg of LPS and 50 mg/kg of sodium glycocholate respectively was administered twice into the abdomen of mice, respectively. While all mice in the negative control group died before 60 hours passed after the administration of LPS into the abdomen, the experimental group in which 12.5 mg/kg and 50 mg/kg of sodium glycocholate was administered after 1 hour and 6 hours from the administration of LPS respectively, showed that the survival rate of the mice was 40% and 60% respectively (FIG. 17).

EXAMPLE 8

Assay of the Inhibition of the In Vivo Generation of Anti-Inflammatory Cytokine by LPS As described in Example 7, 20 mg/kg of LPS was administered into the abdomen of mice and then 12.5 mg/kg of sodium glycocholate, and 20 mg/kg of LPS and 50 mg/kg of sodium glycocholate respectively was administered twice into the abdomen of mice, respectively. At the predetermined time, blood was collected from mouse tail and then serum was obtained by centrifugation (2400×g, 10 min). The change of cytokine expression in the serum was measured by using cytometric bead array (CBA) kit.

Figure 18:
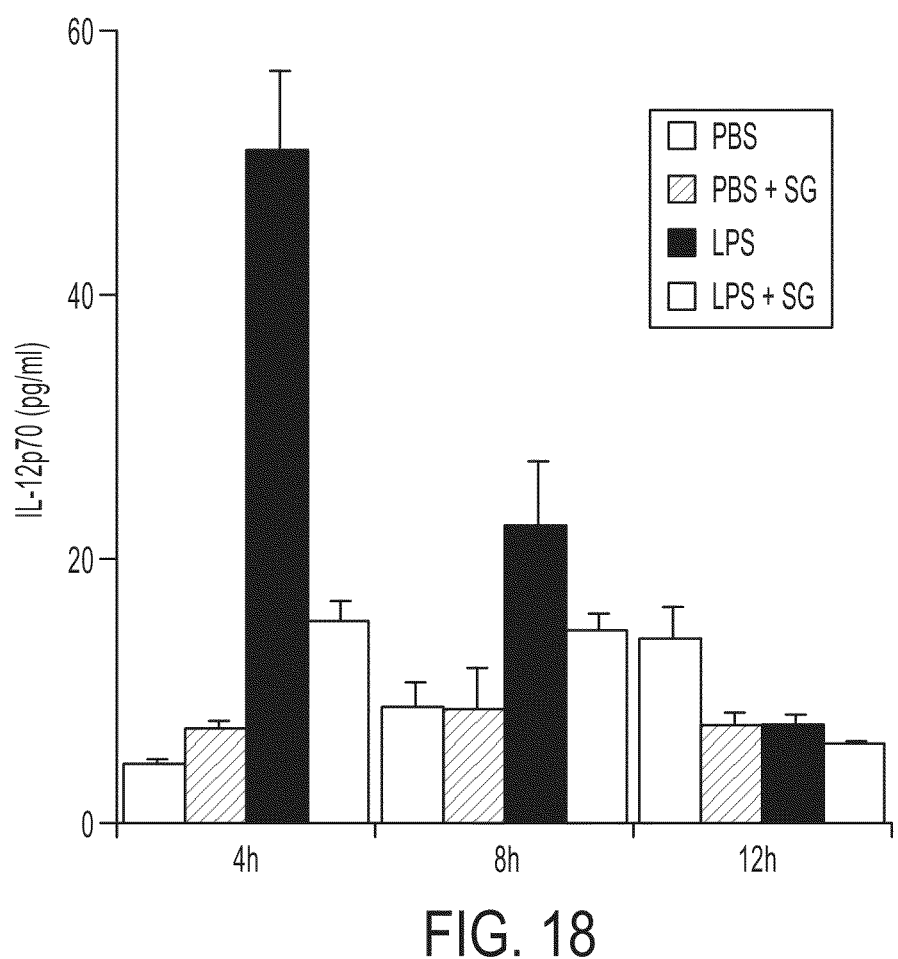
FIG. 18 shows a decrease of IL-12p70, a proinflammatory cytokine, when sodium glycocholate is administered to an LPS-administered C57BL/6 mouse in Example 8 of the present invention.
Figure 19:
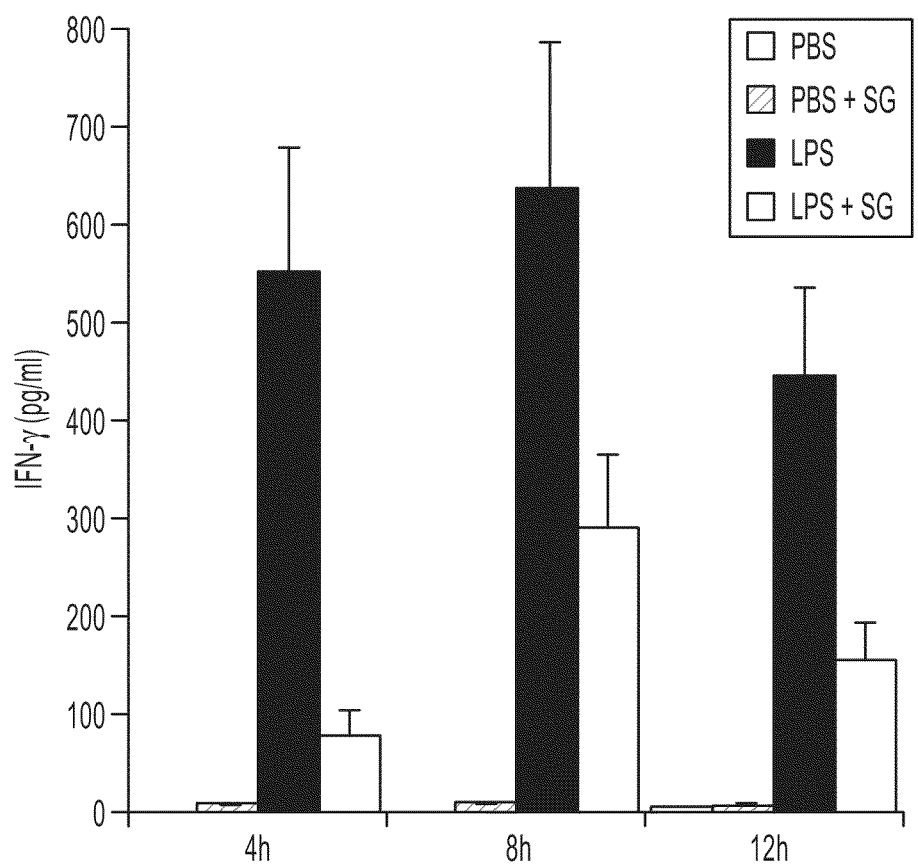
FIG. 19 shows a decrease of IFN-g, a proinflammatory cytokine, when sodium glycocholate is administered to an LPS-administered C57BL/6 mouse in Example 8 of the present invention.
Figure 20:
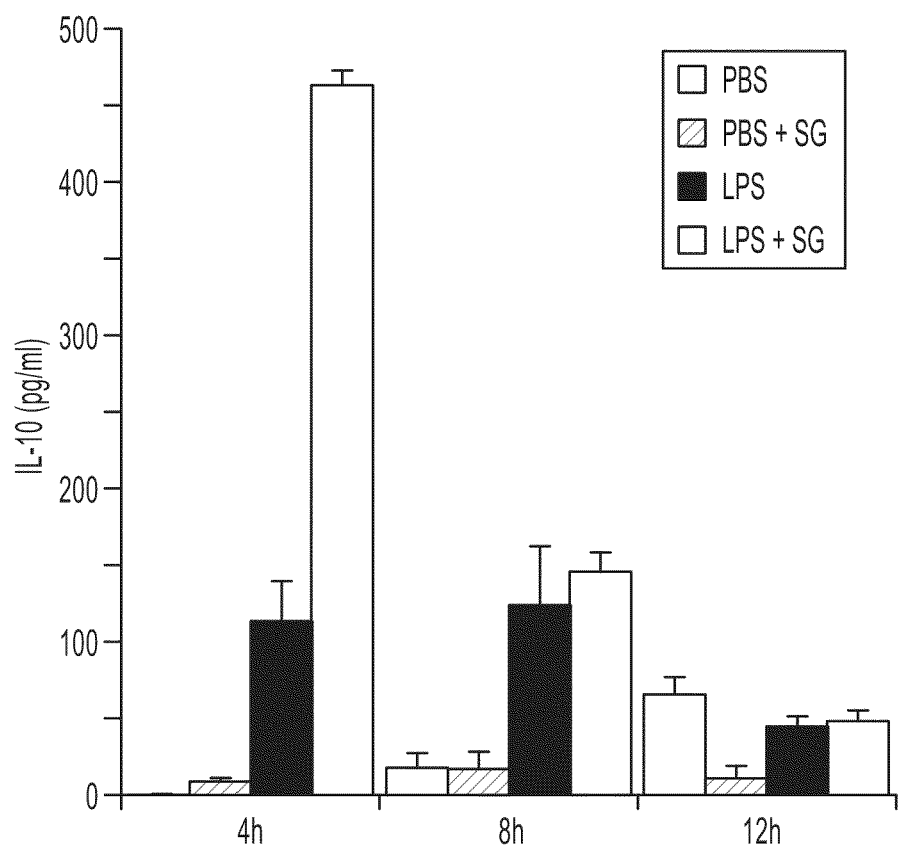
FIG. 20 shows an increase of IL-10, an anti-inflammatory cytokine, when sodium glycocholate is administered to an LPS-administered C57BL/6 mouse in Example 8 of the present invention.
Figure 21:
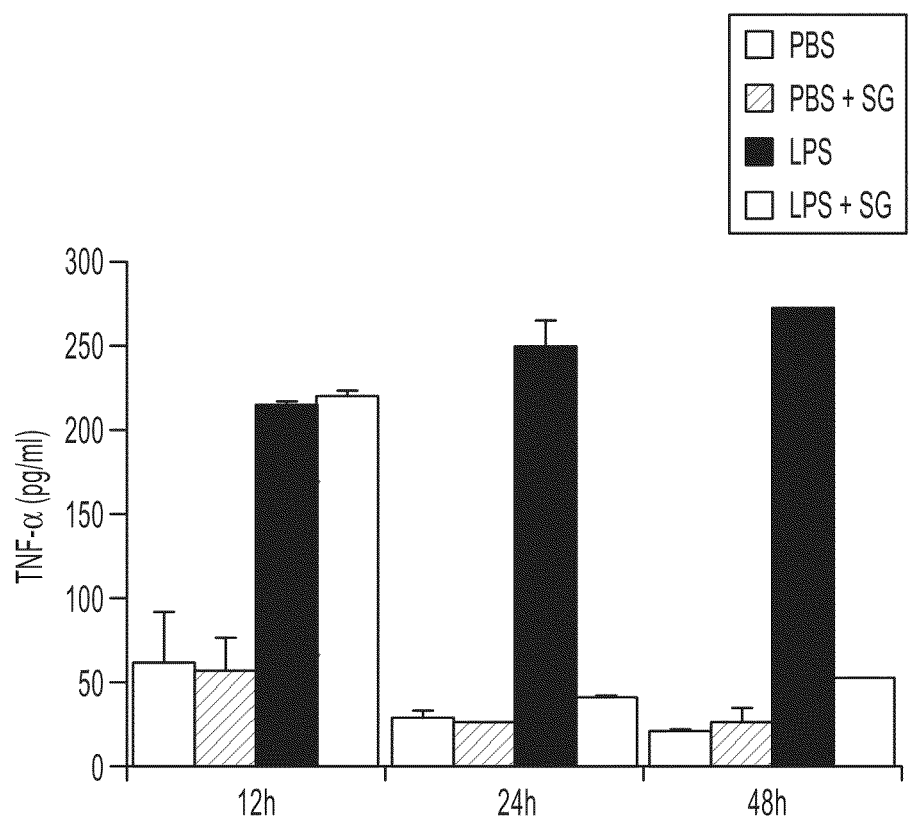
FIG. 21 shows a decrease of TNF-α, a proinflammatory cytokine, when sodium glycocholate is administered to an LPS-administered C57BL/6 mouse in Example 8 of the present invention.
Figure 22:
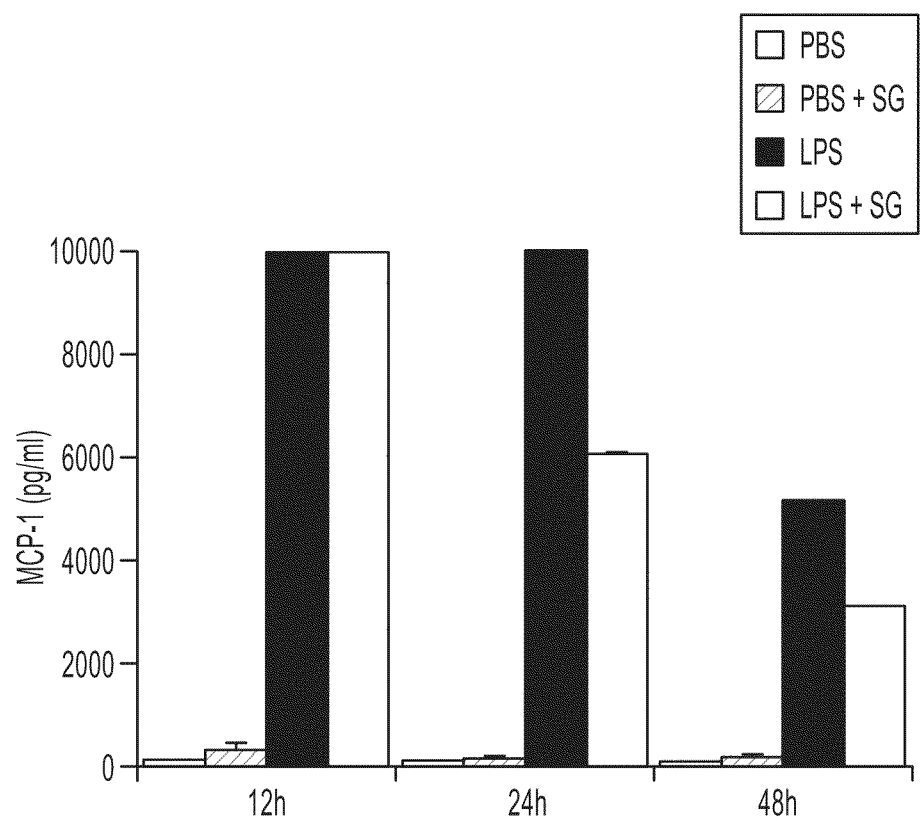
FIG. 22 shows a decrease of MCP-1, a proinflammatory cytokine, when sodium glycocholate is administered to an LPS-administered C57BL/6 mouse in Example 8 of the present invention.
Figure 23:
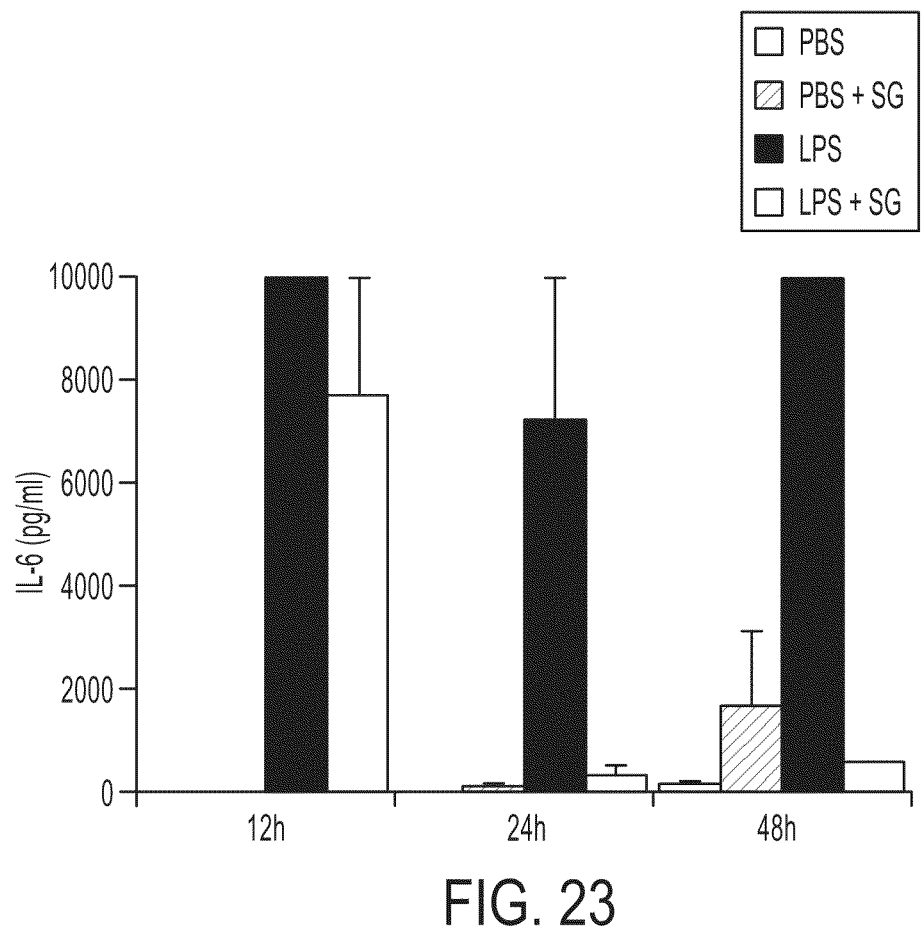
FIG. 23 shows a decrease of IL-6, a proinflammatory cytokine, when sodium glycocholate is administered to an LPS-administered C57BL/6 mouse in Example 8 of the present invention.

IL-12p70 and IFN-g were decreased after 4 hours, 8 hours and 12 hours from the administration of sodium glycocholate (FIG. 18 and FIG. 19), and TNF-α, MCP-1 and IL-6 were remarkably decreased after 12 hours, 24 hours and 48 hours from the administration of sodium glycocholate (FIG. 21, FIG. 22 and FIG. 23). IL-10 which is a anti-inflammatory cytokine significantly increased in the experimental group to which sodium glycocholate was administered (FIG. 20).

EXAMPLE 9

Assay of the Anti-Inflammatory Effect of Sodium Glycocholate as an Preservative Solution Additive for Organ Transplantation The effect of sodium glycocholate to inflammatory response and renal function in an ischemia-reperfusion renal injury model, was evaluated. Five Sprague-Dawley (SD) male rats of 6 weeks age were used per each group, and foods and waters were not supplied to all the rats from 1 day before the experiment. The rats were anesthetized by the administration of 1 mg avertin (tribromoethanol/amyl hydrate)/100 g rat to the abdomen of the rats, and then laparotomized. All the blood flow to a left kidney was blocked by clamping the aorta and vena cava using vascular clamps. Before injecting the organ preservative solution, a vein of the left kidney was penetrated to minimize physical damage of the kidney due to the preservative solution pressure. Then, after histidine-tyroptophan-ketoglutarate (HTK) or a mixture solution of HTK and 0.5 mg/ml of sodium glycocholate was injected, at 4 ml/rat, into the vein, the damaged part of the vein was sutured by using 10-0 suture. After 30 min maintenance of the above state, the vascular clamps were removed and the laparotomized part was sutured. After 24 hour reperfusion, the operated rat was anesthetized again, and blood was sampled from the heart to prepare plasma or serum. Sham operation group was operated in the same way as the above except the treating procedure of HTK or sodium glycocholate containing HTK solution (HTKN), and all the operation was repeated at least three times. The concentration of IL-6 in the serum was measured by a enzyme-linked immunosorbent assay, and the concentrations of blood urea nitrogen (BUN), creatinine (Cre) and aspartate aminotransferase (AST) in the plasma were measured by an automated analyzer.

Figure 24:
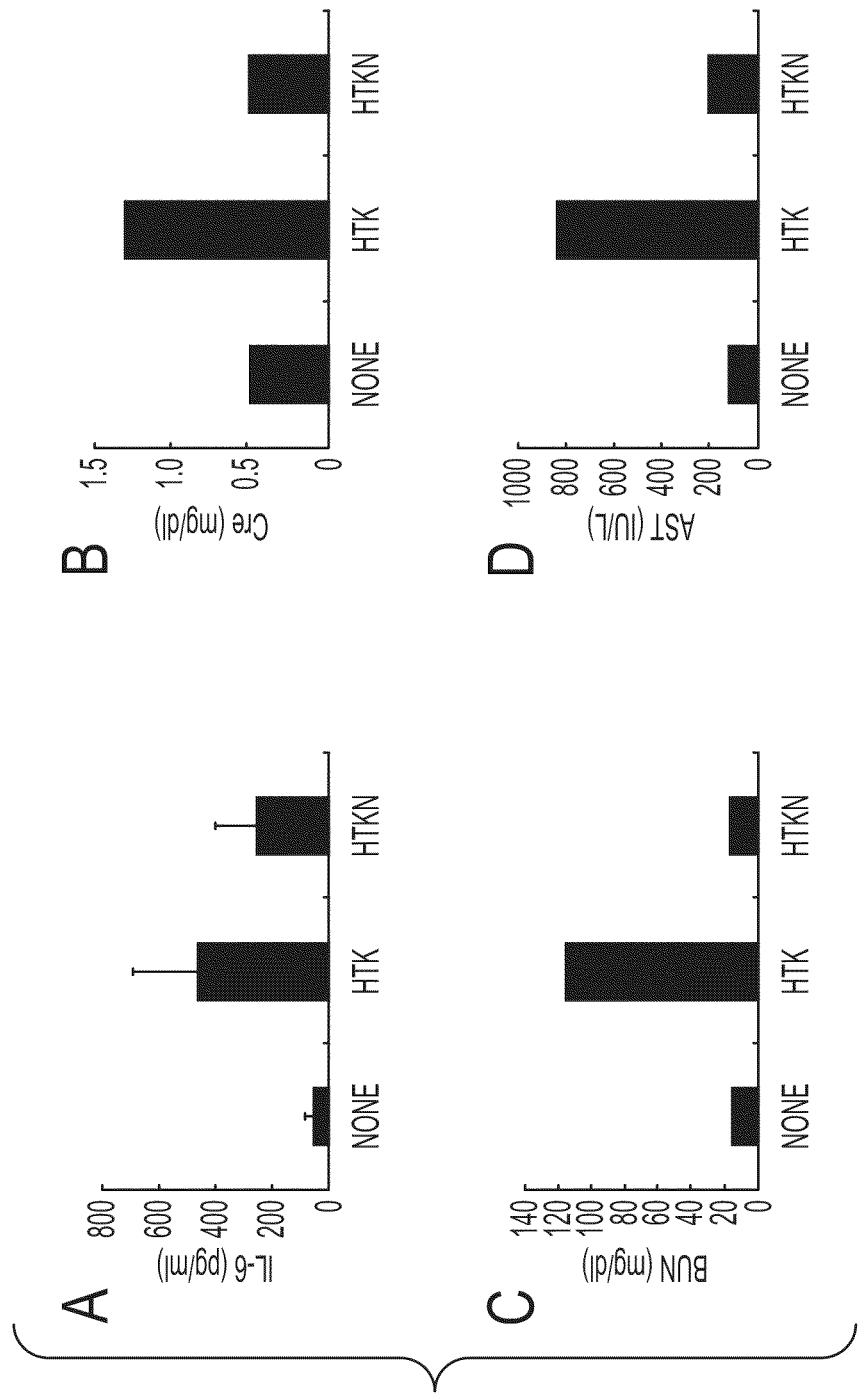
FIG. 24 shows an influence of sodium glycocholate for the inflammatory response and kidney function in the case of ischemia-reperfusion injury in kidney.

For ischemia-reperfusion injury, the concentration of IL-6 in the experimental group treated with HTK solution was 466±218 pg/ml, and the concentration of IL-6 in the experimental group treated with HTKN solution was 260±144 pg/ml (p=0.08 compared with the experimental group treated with HTK solution). Consequently, it was confirmed that inflammatory response was inhibited (FIG. 24). In addition, the concentrations of BUN, Cre and AST, which are the indication of renal function, in the HTK treated group were significantly lower than those in the HTKN treated group, which indicates that sodium glycocholate inhibited the ischemia-reperfusion renal injury (FIG. 24).

EXAMPLE 10

Assay of Toxicity

The cytotoxicity of sodium glycocholate to the CHO cells, dendritic cells, T cells which were used in the above Examples was assayed. FACS analysis was performed after staining with 7AAD. First, sodium glycocholate was kept in vitro for 1 hour at 37° C., and then mixed with cells. CHO cells or dendritic cells were incubated for 14 hours at 37° C., and T cells which were mixed with 14 hour-incubated dendritic cells, were incubated for 4 days. Then, each cell was stained with 7AAD and cell analysis were carried out by using a flow cytometer.

In order to assay the toxicity of sodium glycocholate to a mouse, experiments were performed to five C57BL/6 male mice of 7-9 weeks age per each group. Sodium glycocholate dissolved in PBS was kept in vitro for 1 hour at 37° C., and then the sodium glycocholate solution was administered into the abdomen of the mice followed by the cell analysis. After 1 hour from the administration, the abdominal cells were separated and stained with 7AAD, and then the abdominal cells were analyzed. Cells which were freezed and thawed at least five times were used for a positive control group in 7ADD staining. Experimental results were statistically analyzed by t-test, and $p<0.05$ compared with the experimental group which was not treated with sodium glycocholate.

7AAD(+) of CHO cells (FIG. 25A), dendritic cells (FIG. 25B) and dendritic cell-mediated T cells (FIG. 25C) was increased by 2-4% under the presence of sodium glycocholate, compared with the negative control group, and 1 mg/ml of sodium glycocholate showed no significant cytotoxicity (FIG. 25). It was also confirmed that the survival rate of the abdominal cells which were separated the mouse administered with 5 mg sodium glycocholate/rat (250 mg/kg rat), showed no significant difference from that of the control group administered only PBS (FIG. 25D).

Figure 25B:
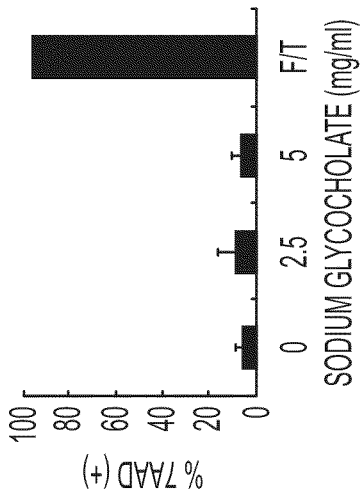
FIG. 25B shows that sodium glycocholate dose not have cytotoxicity for a dendritic cell treated therewith in Example 10 of the present invention.
Figure 25D:
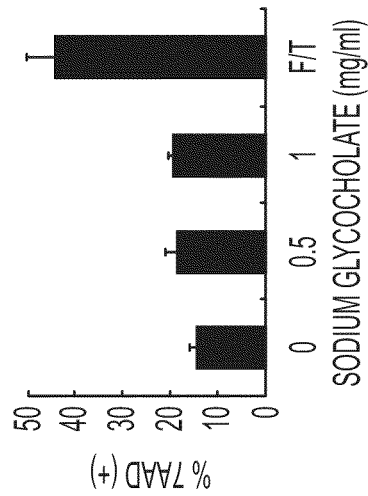
FIG. 25D shows that sodium glycocholate dose not have cytotoxicity for an abdominal cell separated from the mouse treated therewith in Example 10 of the present invention.
Figure 25A:
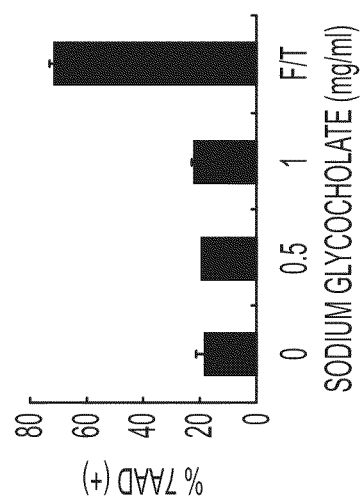
FIG. 25A shows that sodium glycocholate dose not have cytotoxicity for a CHO cell treated therewith in Example 10 of the present invention.
Figure 25C:
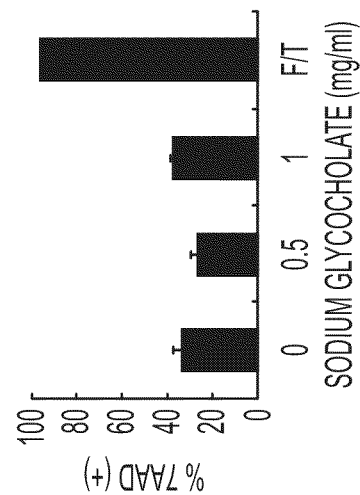
FIG. 25C shows that sodium glycocholate dose not have cytotoxicity for a dendritic cell-mediated T cell treated therewith in Example 10 of the present invention.
Figures 26A, 26B:
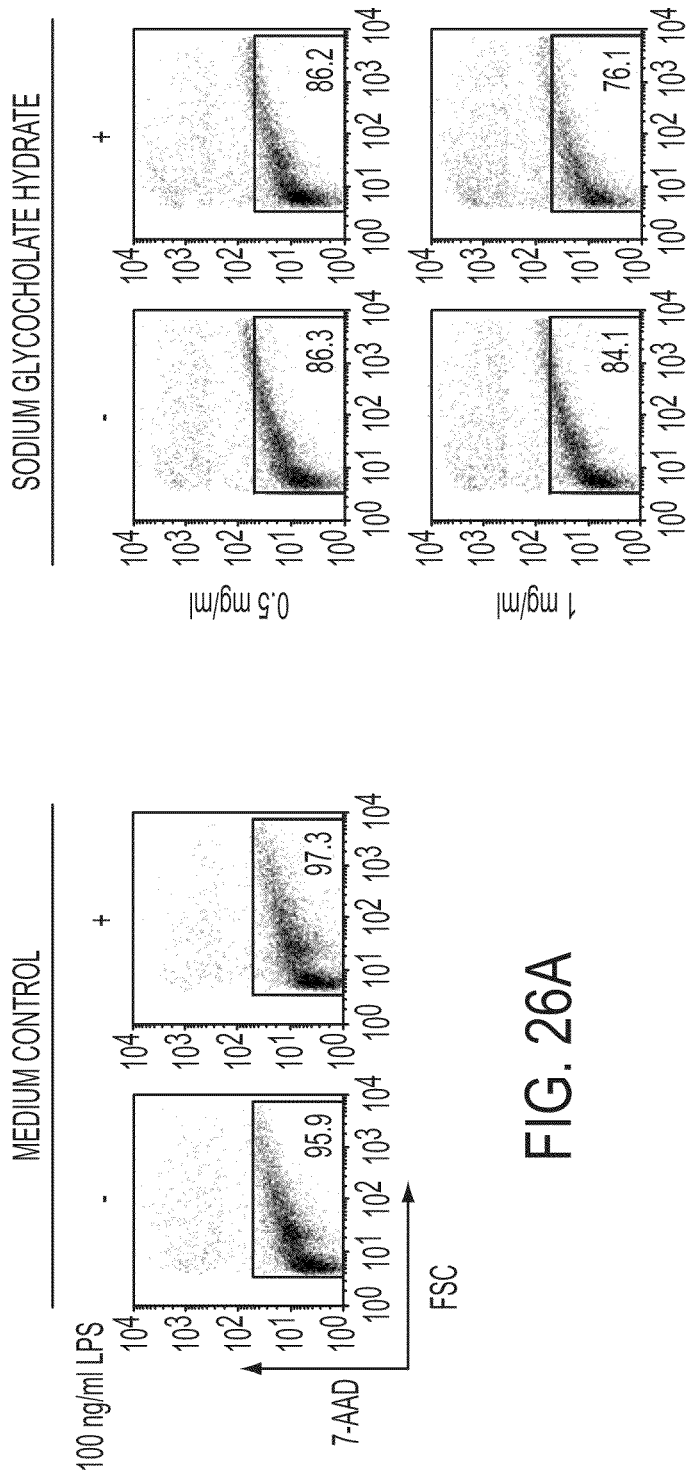
FIGS. 26A-26C show cytotoxicity of sodium glycocholate hydrate and sodium deoxycholate for a CHO cell in Example 10 of the present invention.
Figure 26C:
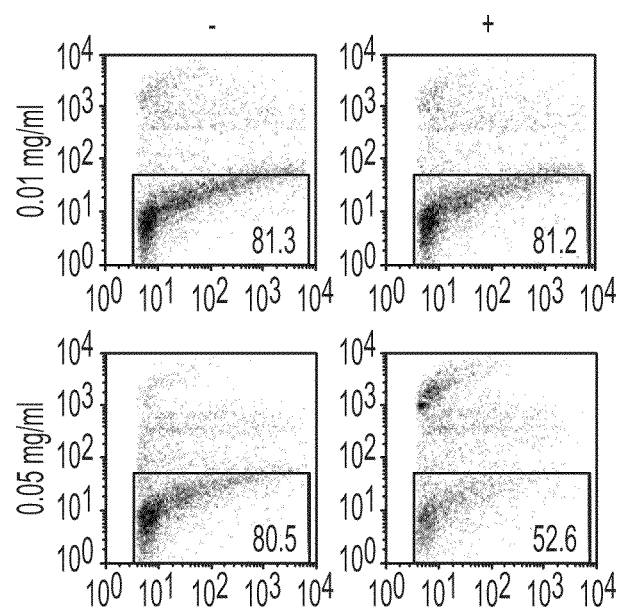
Figures 27A, 27B:
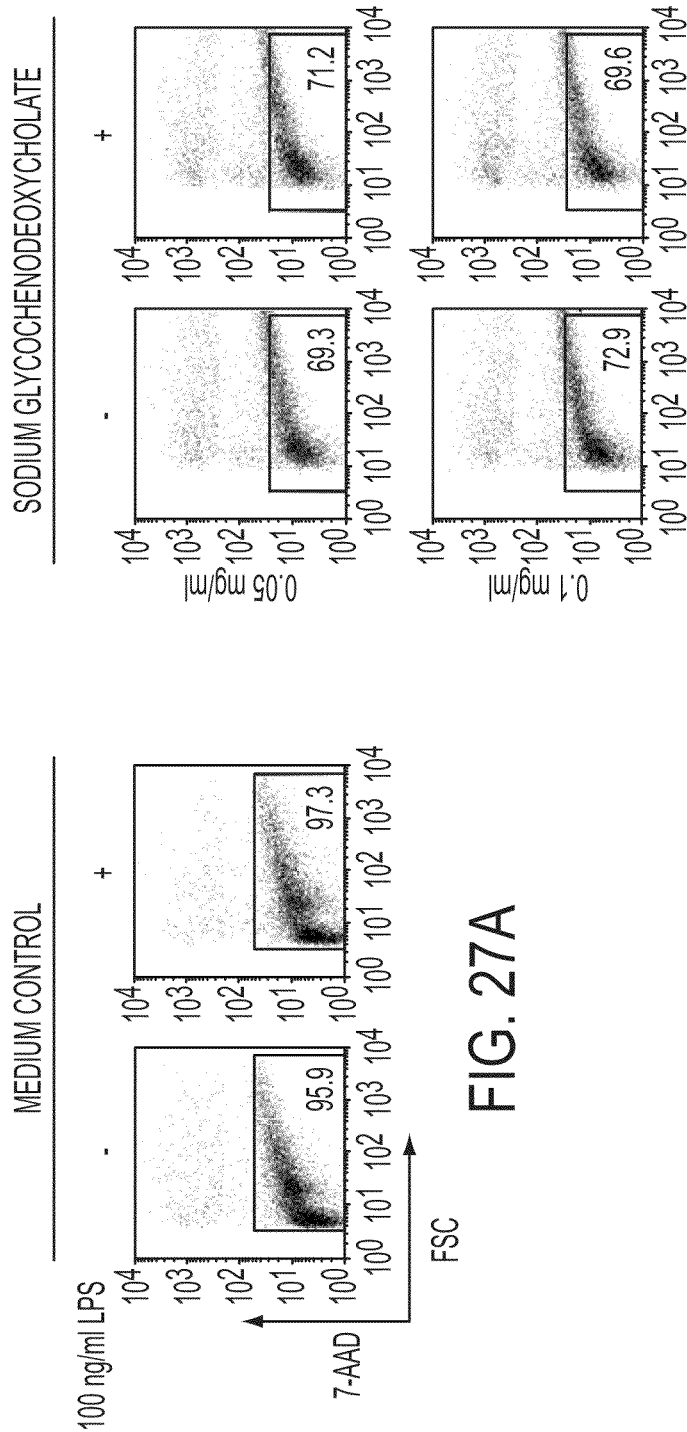
FIGS. 27A-27C show cytotoxicity of sodium glycochenodeoxycholate and sodium taurochenodeoxycholate for a CHO cell in Example 10 of the present invention.
Figure 27C:
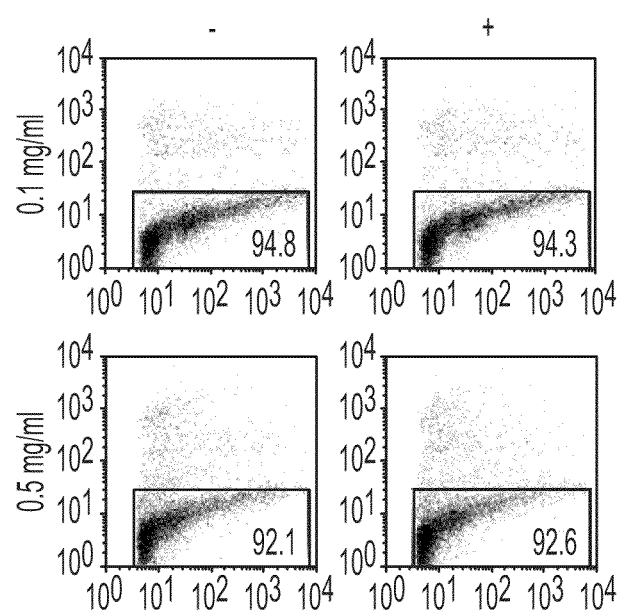
Figures 28A, 28B:
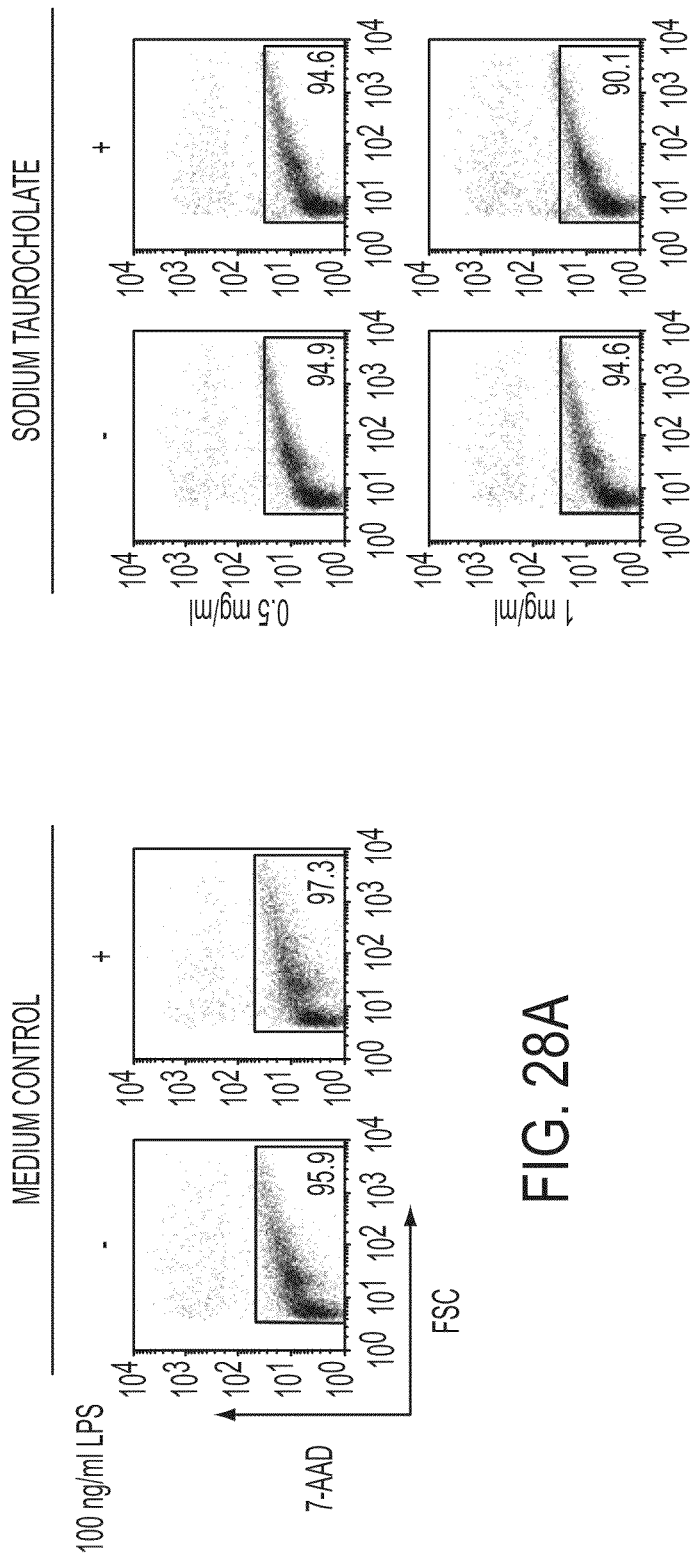
FIGS. 28A-28C show cytotoxicity of sodium taurocholate and sodium taurodeoxycholate for a CHO cell in Example10 of the present invention.
Figure 28C:
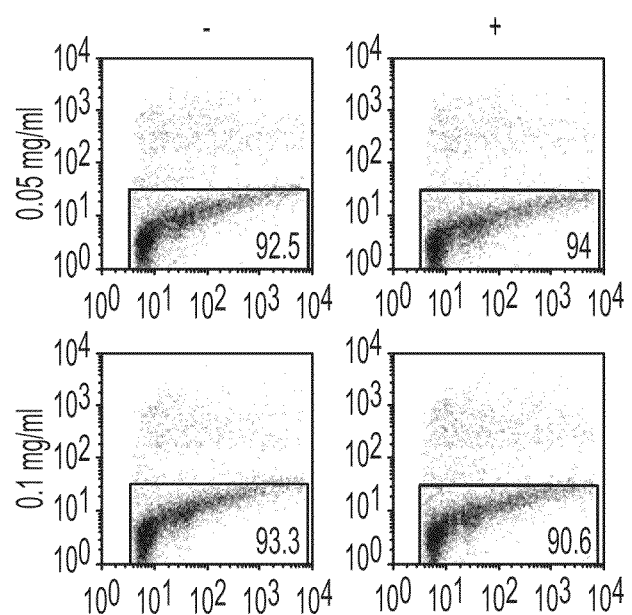
Figures 29A, 29B:
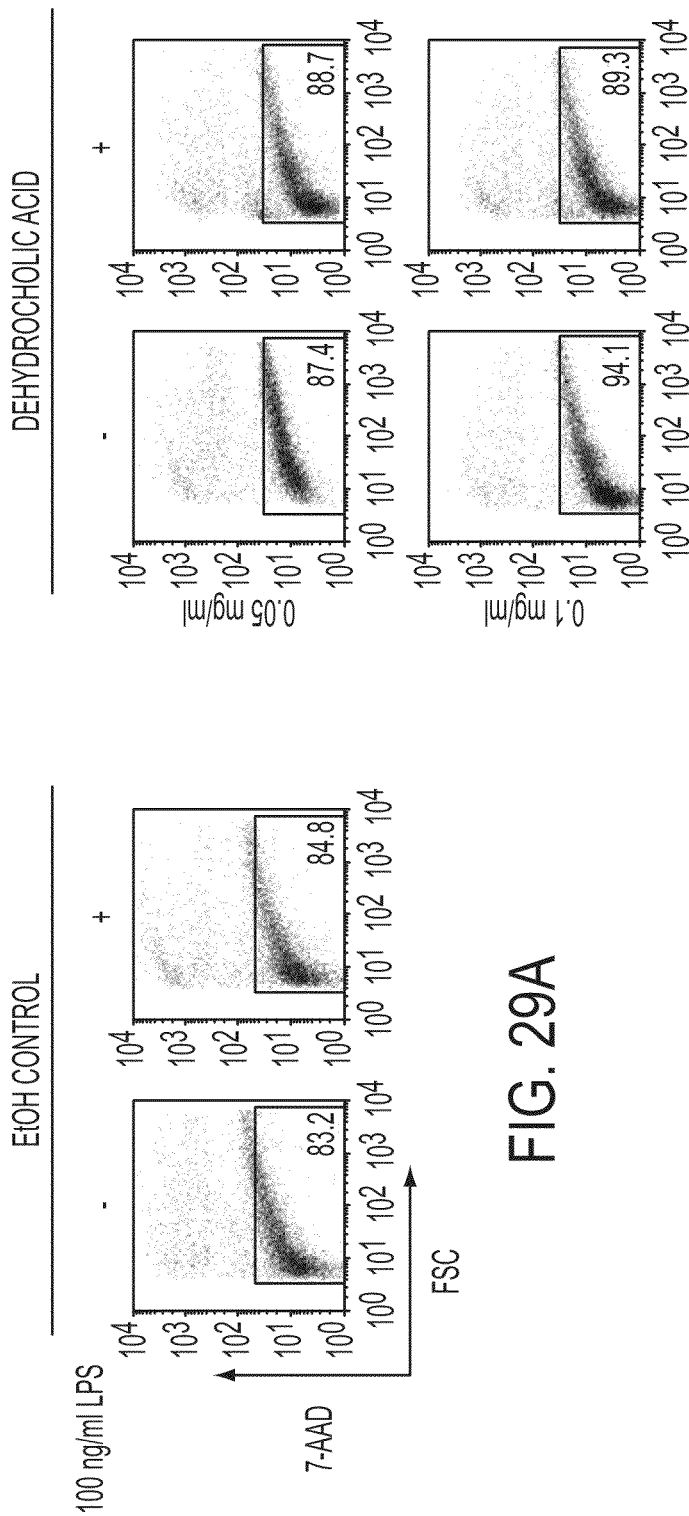
FIGS. 29A-29C show cytotoxicity of dehydrocholic acid and lithocholic acid for a CHO cell in Example 10 of the present invention.
Figure 29C:
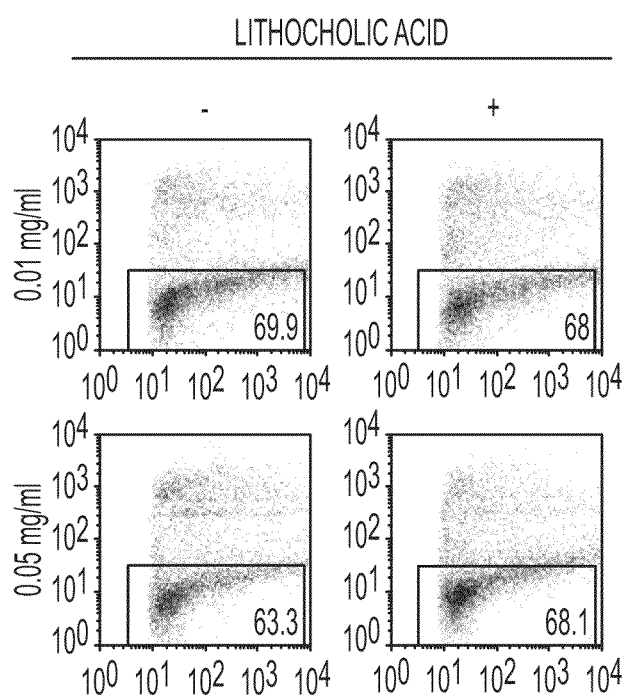
Figure 30C:
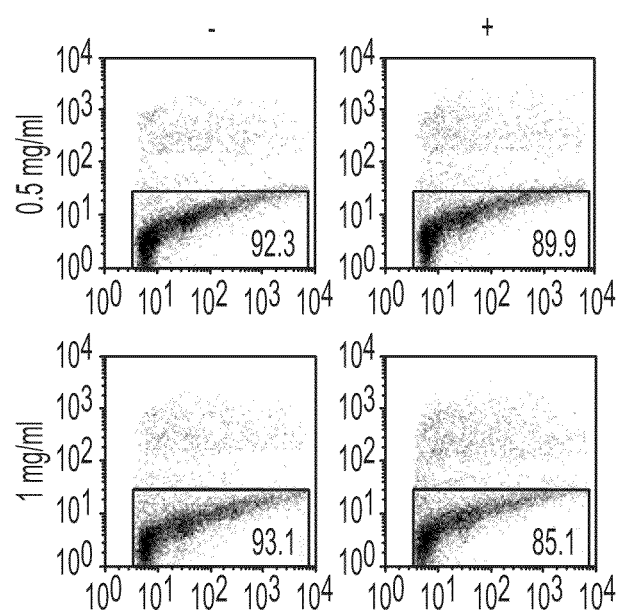
Figures 31A, 31B:
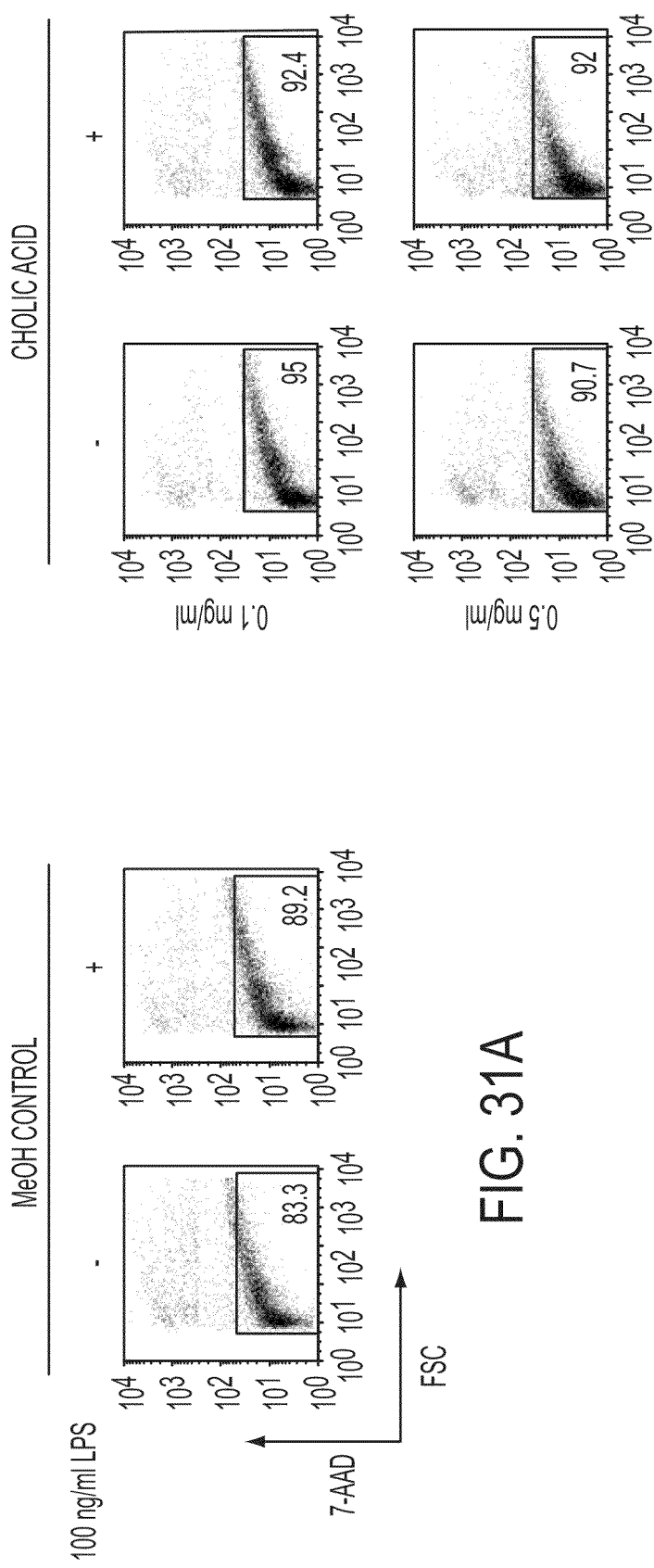
FIGS. 31A-31B show cytotoxicity of cholic acid for a CHO cell in Example 10 of the present invention.

The same procedures as for FIG. 25A were carried out in FIGS. 26A-26C-Figs. 31A-31B and cytotoxicity experiments were performed on three groups of bile acid derivatives which were classified based on their solubility in different solvents. Comparing with negative control groups of each solvent, no significant cytotoxicity was shown by water-soluble bile acid derivatives, ethanol-soluble bile acid derivatives and methanol-soluble bile acid derivative.

Figure 32A:
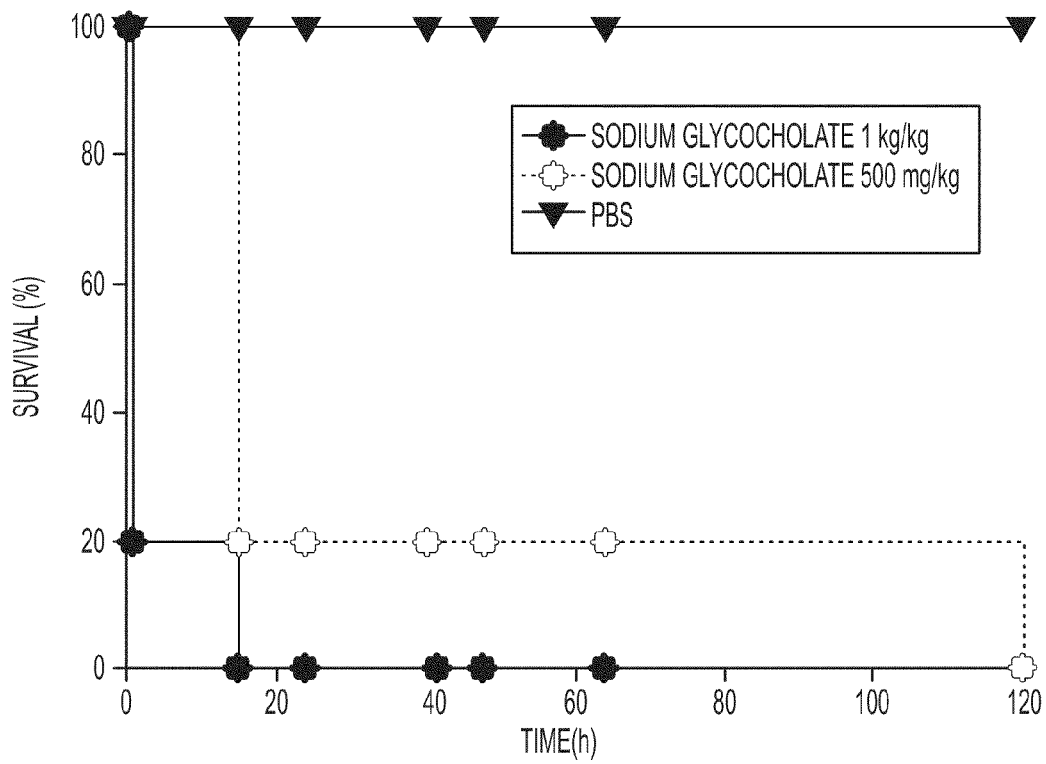
FIGS. 32A-32B show0 cytotoxicity of sodium glycocholate for a Balb/c mouse administered intraabdominally with sodium glycocholate in Example 10 of the present invention.
Figure 32B:
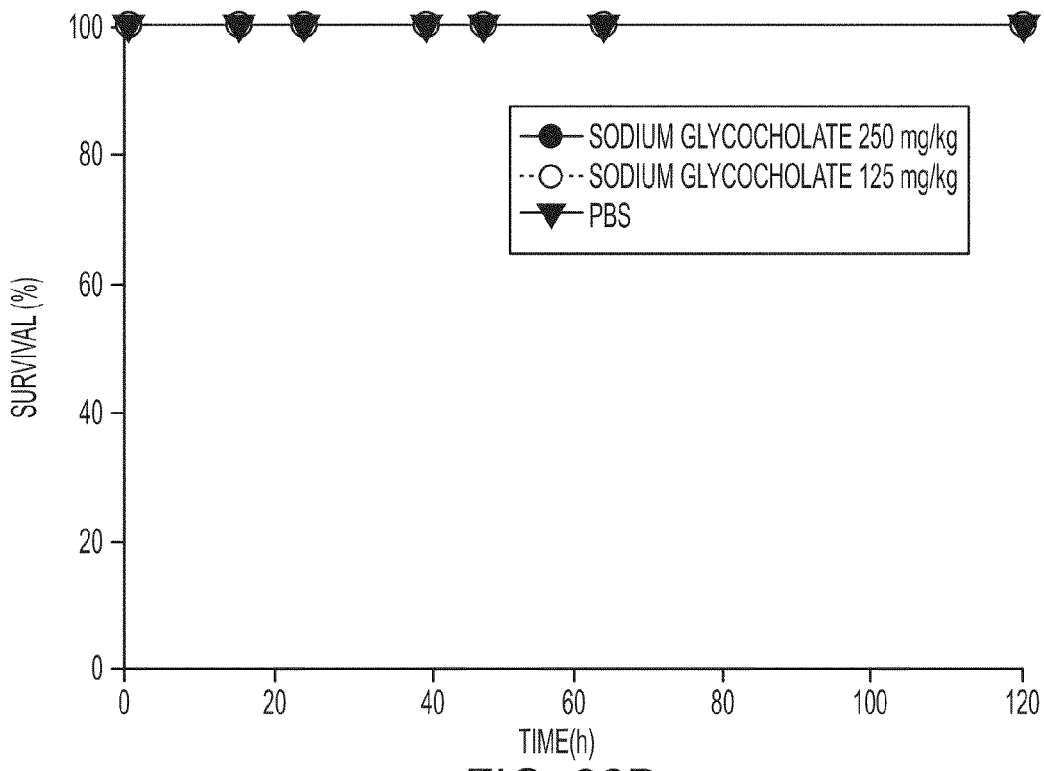
Figure 33:
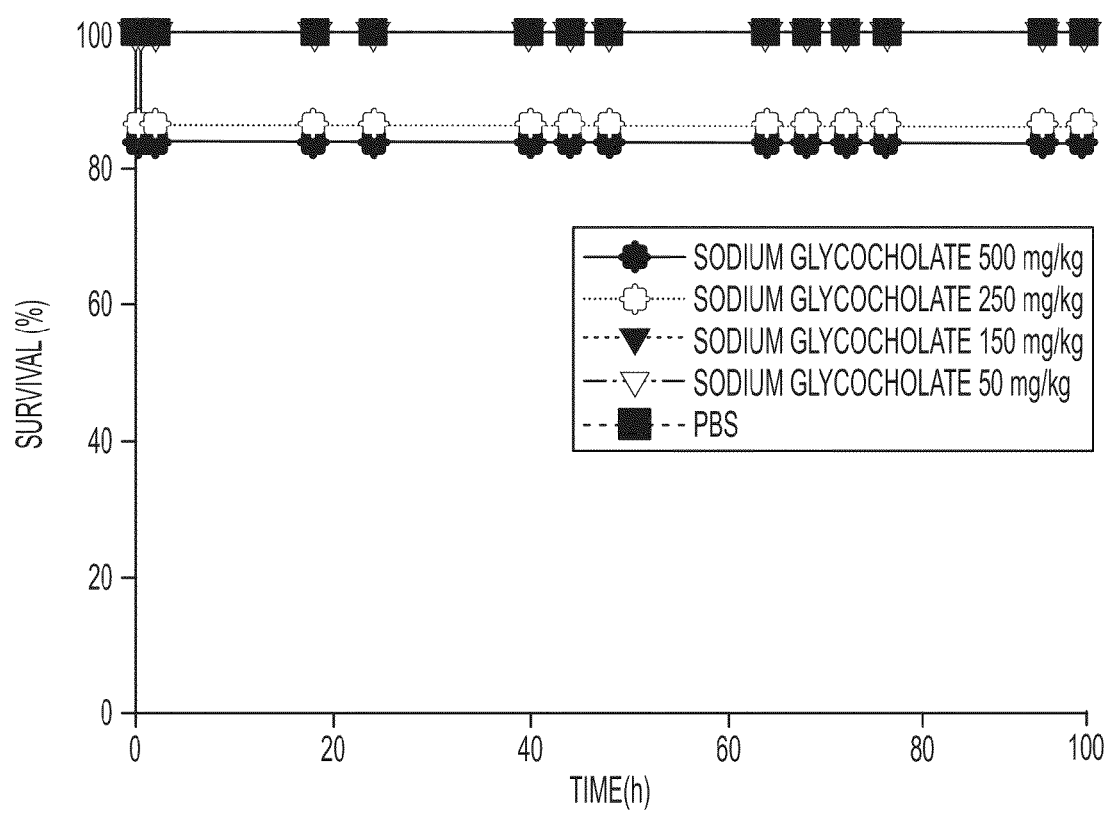
FIG. 33 shows cytotoxicity of sodium glycocholate for a Balb/c mouse when sodium glycocholate was administered through tail vein of the mouse in Example 10 of the present invention.

Acute toxicity was measured by using five Balb/c mice of 6 weeks age per group, which were once administered with sodium glycocholate, at different sodium glycocholate concentrations, into the abdomen and tail vein. In the abdomenal administration experiment, sodium glycocholate showed toxicity at the sodium glycocholate concentration of more that 500 mg/kg. However, 250 mg/kg of sodium glycocholate at which the above-mentioned effects of sodium glycocholate, and the sodium glycocholate concentration of below 250 mg/kg, 100 % of the mice survived (FIGS. 32A-32B). Also, 100 % of the mice survived at the sodium glycocholate concentration of not exceeding 150 mg/kg in the experiment where sodium glycocholate of different concentrations was adiministered into tail vein of mice (FIG. 33).

The invention claimed is:

1. A method of treating sepsis, said method comprising administration to a patient in need of such treatment of a non-toxic, therapeutically effective amount of at least one chemical selected from the group consisting of sodium glycocholate, sodium taurodeoxycholate and sodium glycodeoxycholate.

2. A method of claim 1, wherein the administration route of said at least one chemical is parenteral or injection route.

3. A method of claim 1, wherein the formulation of said at least one chemical is a liquid solution or a suspension.

\* \* \* \* \*